(12) United States Patent
Nakajima et al.

(10) Patent No.: US 11,812,774 B2
(45) Date of Patent: Nov. 14, 2023

(54) COMPOSITION FOR BROWNING INHIBITION AND USE OF SAME

(71) Applicant: SUNTORY HOLDINGS LIMITED, Osaka (JP)

(72) Inventors: Suguru Nakajima, Kyoto (JP); Yumi Sasanuma, Kyoto (JP); Yoshihide Matsuo, Kyoto (JP)

(73) Assignee: SUNTORY HOLDINGS LIMITED, Osaka (JP)

( * ) Notice: Subject to any disclaimer, the term of this patent is extended or adjusted under 35 U.S.C. 154(b) by 1146 days.

(21) Appl. No.: 16/311,851

(22) PCT Filed: Jun. 23, 2017

(86) PCT No.: PCT/JP2017/023317
§ 371 (c)(1),
(2) Date: Dec. 20, 2018

(87) PCT Pub. No.: WO2017/222078
PCT Pub. Date: Dec. 28, 2017

(65) Prior Publication Data
US 2019/0254316 A1 Aug. 22, 2019

(30) Foreign Application Priority Data
Jun. 24, 2016 (JP) ................... 2016-125225

(51) Int. Cl.
| | |
|---|---|
| *A23L 3/3544* | (2006.01) |
| *A23L 3/3481* | (2006.01) |
| *A23L 5/20* | (2016.01) |
| *A23L 29/00* | (2016.01) |
| *A23F 3/16* | (2006.01) |
| *A61K 8/49* | (2006.01) |
| *A61K 8/60* | (2006.01) |
| *A61K 47/22* | (2006.01) |
| *C07D 311/04* | (2006.01) |
| *C09K 3/00* | (2006.01) |

(52) U.S. Cl.
CPC ............ *A23L 3/3544* (2013.01); *A23F 3/16* (2013.01); *A23L 3/3481* (2013.01); *A23L 5/27* (2016.08); *A23L 29/00* (2016.08); *A23V 2002/00* (2013.01); *A23V 2200/048* (2013.01); *A61K 8/49* (2013.01); *A61K 8/60* (2013.01); *A61K 47/22* (2013.01); *C07D 311/04* (2013.01); *C09K 3/00* (2013.01)

(58) Field of Classification Search
CPC ........ A23L 3/2544; A23L 5/27; A23L 3/3544; A23F 3/16
See application file for complete search history.

(56) References Cited

U.S. PATENT DOCUMENTS

| | | | | |
|---|---|---|---|---|
| 6,036,991 A | * | 3/2000 | Humphrey | ............... A23F 3/14 |
| | | | | 426/597 |
| 2004/0091589 A1 | * | 5/2004 | Roy | ....................... A23L 5/47 |
| | | | | 426/265 |

(Continued)

FOREIGN PATENT DOCUMENTS

| | | |
|---|---|---|
| CN | 104 906 023 A | 9/2015 |
| DE | 3617305 A1 | 11/1986 |

(Continued)

OTHER PUBLICATIONS

Bruzewicz, S., Malicki, A., Oszmianski, J., Jaroslawska, A., and Jarmoluk, A., "Baicalin, Added as the Only Preservative, Improves the Microbiological Quality of Homemade Mayonnaise," Pakistan Journal of Nutrition, 5 (1): 30-33 (2006) (Year: 2006).*
Liang, R., Han, R., Fu, L., Ai., X., Zhang, J., Skibsted, L., "Baicalin in Radical Scavenging and Its Synergistic Effect with β-Carotene in Antilipoxidation," J. Agric. Food Chem., 2009, 57, 7118-7124 (Year: 2009).*
Wang, C., Mehendale, S., and Yuan, C., "Commonly Used Antioxidant Botanicals: Active Constituents and their Potential Role in Cardiovascular Illness," Am J Chin Med, 2007, 35(4): 543-558 (Year: 2007).*

(Continued)

*Primary Examiner* — Jeffrey P Mornhinweg
(74) *Attorney, Agent, or Firm* — WHDA, LLP

(57) ABSTRACT

The present invention relates to a browning-inhibiting composition containing a compound represented by the following formula (1):

[Chem. 1]

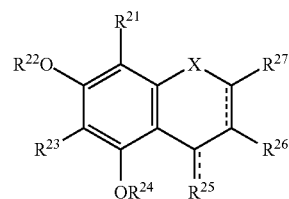

(1)

wherein $R^{21}$, $R^{22}$, $R^{23}$, $R^{24}$, $R^{26}$ and $R^{27}$ each independently represent a hydrogen atom or a substituent, and at least one of $R^{21}$ or $R^{23}$ is a hydrogen atom; when $R^{23}$ represents a hydrogen atom, at least one of $R^{22}$ or $R^{24}$ represents a substituent; $R^{25}$ represents a hydrogen atom, an oxygen atom, or a substituent; $R^{22}$ and $R^{23}$, or $R^{23}$ and $R^{24}$ may be bonded together to form a ring with an oxygen atom and a carbon atom to which these Rs are bonded; $R^{25}$ and $R^{26}$, or $R^{26}$ and $R^{27}$ may be bonded together to form a ring structure with carbon atoms to which these Rs are bonded; X represents an oxygen atom or —$CH_2$—; and a dashed line may represent a double bond.

5 Claims, 9 Drawing Sheets

(56) References Cited

U.S. PATENT DOCUMENTS

| | | | |
|---|---|---|---|
| 2011/0064846 A1 | 3/2011 | Ho et al. | |
| 2012/0029183 A1* | 2/2012 | Ishida | A61P 37/00 536/122 |

FOREIGN PATENT DOCUMENTS

| | | |
|---|---|---|
| JP | 61-268259 A | 11/1986 |
| JP | 1-289446 A | 11/1989 |
| JP | H3-240725 A | 10/1991 |
| JP | 5-276883 A | 10/1993 |
| JP | 2000-319154 A | 11/2000 |
| JP | 2004-091338 A | 3/2004 |
| JP | 2006-248832 A | 9/2006 |
| JP | 2007-267724 A | 10/2007 |
| JP | 2007-325588 A | 12/2007 |
| JP | 2008-92869 A | 4/2008 |
| JP | 2008-289438 A | 12/2008 |
| JP | 2009-517461 A | 4/2009 |
| JP | 2011-37738 A | 2/2011 |
| JP | 2012-125217 A | 7/2012 |
| JP | 2012-521424 A | 9/2012 |
| JP | 2012-219076 A | 11/2012 |
| JP | 2013-146211 A | 8/2013 |
| JP | 2016-88887 A | 5/2016 |
| WO | 2007/064085 A1 | 6/2007 |
| WO | 2010/110993 A2 | 9/2010 |
| WO | 2013/093730 A1 | 6/2013 |

OTHER PUBLICATIONS

Curiel, J.A. et al., "Delaying Effect of a Wine Lactobacillus plantarum Strain on the Coloration and Xanthylium Pigment Formation Occurring in (+)-Catechin and (−)-Epicatechin Wine Model Solutions", Journal of Agricultural and Food Chemistry, 2010, vol. 58, No. 21, pp. 11318-11324, cited in JP Office Action dated Sep. 28, 2021. (7 pages).

Extended Search Report dated Jan. 9, 2020, issued in counterpart EP Application No. 17815543.8 (14 pages).

Takahashi, Tetsuya et al., "Synergetic deodorant effect and antibacterial activity of composite paper containing waste tea leaves", Journal of Wood Science, 2011, 57, pp. 308-316; Cited in EESR dated Jan. 9, 2020.

Gujer, R. et al, "Glucosylated Flavonoids and Other Phenolic Compounds from Sorghum", Phytochemistry, 1986, vol. 25, No. 6, pp. 1431-1436; cited in ISR.

George, N. et al, "Factors influencing the production and stability of xanthylium cation pigments in a model white vine system", Australian Journal of Grape and Wine Research, 2006, vol. 12, pp. 57-68; cited in ISR.

Es-Safi, N-E., "Colour of a xanthylium pigment in aqueous solutions at different pH values", Food Chemistry, 2004, vol. 88, pp. 367-372; cited in ISR.

Es-Safi, N-E. et al, "New Phenolic Compounds Formed by Evolution of (+)-Catechin and Glyoxylic Acid in Hydroalcoholic Solution and Their Implication in Color Changes of Grape-Derived Foods", J. Agric. Food Chem., 2000, vol. 48, pp. 4233-4240; cited in ISR and in the Specification.

Schulz, A. et al., "Electrospray ionization mass spectrometric investigations of α-dicarbonyl compounds—Probing ntermediates formed in the course of the nonenzymatic browning reaction of L-ascorbic acid", International Journal of Miass Spectrometry, 2007, vol. 262, pp. 169-173; cited in ISR.

Li, H. et al, "Mechanisms of oxidative browning of wine", Food Chemistry, 2008, vol. 108, pp. 1-13; cited in the Specification.

Barril, C. et al., "Understanding the contribution of ascorbic acid to the pigment development in model while wine systems using liquid chromatography with diode array and mass spectrometry detection techniques", Analytica Chimica Acta, 2008, vol. 621, pp. 44-51; cited in the Specification.

Es-Safi, N-E, et al, "New Polyphenolic Compounds with Xanthylium Skeletons Formed through Reaction between (+)-Catechin and Glyoxylic Acid", J Agric. Food Chem., 1999, vol. 47, pp. 5211-5217; cited in the Specification.

Fulcrand, H. et al, "Phenolic Reactions during Winemaking and Aging", Am. J. Enology and Viniculture, 2006, vol. 57, No. 3, pp. 289-297; cited in the Specification.

* cited by examiner 6 days  22 days  5 months  7 months  9 months

COMPOSITION FOR BROWNING INHIBITION AND USE OF SAME

TECHNICAL FIELD

The present invention relates to browning-inhibiting compositions and uses of the same. The present invention also relates to methods for inhibiting browning in a polyphenol-containing composition, methods for producing a food or drink product, food or drink products, methods for suppressing reduction of polyphenols in a polyphenol-containing composition, methods for suppressing production of a compound having a xanthylium structure in a polyphenol-containing composition, aldehyde-scavenging compositions, methods for scavenging aldehydes, deodorizing compositions, deodorizing methods, and methods for screening for a compound having a browning-inhibiting effect on a polyphenol-containing composition.

BACKGROUND ART

Commercially available tea beverages such as green tea, Hojicha, and black tea are sterilized and packed in containers such as PET bottles, cans, and paper containers. Tea beverages maybe consumed long after production, and the colors of these liquids are known to turn into brown (hereinafter referred to as "browning") in some cases. Changes in color tone are more noticeable and problematic particularly in green tea beverages than in other beverages because when green tea beverages are stored at room temperature, the tea extract undergoes gradual changes in color from light green or light yellow to yellowish brown to reddish brown. Such browning in tea beverages occurs not only at room temperature but also when the tea extract is heat-sterilized during production of beverages, and further proceeds during storage after production.

Nowadays, clear PET bottles are often used as containers for beverages. Beverages in PET bottles are visible from outside, so that browning impairs the appearance, reducing the product quality.

Such changes in color of beverages presumably occur due to oxidation of components. Thus, in order to inhibit browning in beverages, generally, oxygen is removed by a method such as adding an antioxidant such as ascorbic acid to beverages or removing oxygen from beverages during production. However, materials of PET bottles (i.e., polyethylene terephthalate (PET) resins) are oxygen permeable, and the above methods cannot sufficiently inhibit browning in green tea beverages.

As a technique to inhibit discoloration in food products, for example, Patent Literature 1 discloses a flavonoid composition containing rutin and/or a rutin derivative and dihydroquercetin and/or a dihydroquercetin derivative. According to Patent Literature 1, the composition exerts functions such as antioxidation and fading resistance. According to Patent Literatures 2 and 3, although use of seasonings containing rutin for egg dishes turn the color of the egg yolk from yellow to brown, changes in color tone of food products can be reduced by adding a specific amount of a specific flavonoid to the seasonings. Patent Literature 4 discloses a liquid seasoning containing a phosphoric acid-based compound and a polyphenol having a catechol skeleton at a specific ratio, as a seasoning that does not color foods when used for cooking.

A xanthylium salt formed by a reaction of a catechin with glyoxylic acid derived from tartaric acid has been reported as one cause of browning in white wines (Non-Patent Literatures 1 to 4). Non-Patent Literature 5 discloses the presence of several isomers of a xanthylium salt formed by a reaction of glyoxylic acid with a catechin.

CITATION LIST

Patent Literature

Patent Literature 1: JP 2008-92869 A
Patent Literature 2: JP 2007-267724 A
Patent Literature 3: JP 2007-325588 A
Patent Literature 4: JP 2008-289438 A

Non-Patent Literature

Non-Patent Literature 1: H Li et al., Food Chem 108 (2008), pp. 1-13
Non-Patent Literature 2: C Barril et al., Anal Chim Acta 621(2008), pp. 44-51
Non-Patent Literature 3: NE Es-Safi et al., J Agric Food Chem 47 (1999), pp. 5211-5217
Non-Patent Literature 4: H Fulcrand et al., Am J Enology and Viticulture 57 (2006), pp. 289-297
Non-Patent Literature 5: NE Es-Safi et al., J Agric Food Chem 48 (2000), pp. 4233-4240

SUMMARY OF INVENTION

Technical Problem

As described above, while techniques that inhibit discoloration in food or drink products are examined in Patent Literatures 1 to 4, these patent literatures are silent about inhibition of browning in green tea beverages. Non-Patent Literatures 1 to 5 are also silent about inhibition of browning in green tea beverages. Although a technique is desired that can effectively inhibit browning in green tea beverages, causes of browning in green tea beverages remain unknown.

The present invention was made to solve the above problem, and mainly aims to provide a browning-inhibiting composition and a browning-inhibiting method, which are capable of inhibiting browning in a polyphenol-containing composition such as a green tea beverage.

Solution to Problem

As a result of extensive studies on causes of browning in green tea beverages, the present inventors found that a causative substance of browning is a compound having a xanthylium structure which is produced by reactions of aldehydes generated by degradation of L-ascorbic acid (vitamin C) contained in green tea beverages with catechins. They also found that it is possible to inhibit browning in a polyphenol-containing composition such as a green tea beverage by scavenging aldehydes with the use of a compound that reacts with an aldehyde and that does not substantially produce a compound having a xanthylium structure by the reaction. Such a technique that inhibits browning by scavenging aldehydes is different from techniques that inhibit browning by removing oxygen through addition of an antioxidant, for example. The present inventors conducted further studies based on these findings, and completed the present invention.

The browning-inhibiting composition of the present invention contains a compound represented by the following formula (1):

[Chem. 1]

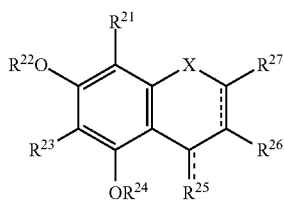

(1)

wherein $R^{21}$, $R^{22}$, $R^{23}$, $R^{24}$, $R^{25}$ and $R^{27}$ each independently represent a hydrogen atom or a substituent, and at least one of $R^{21}$ or $R^{23}$ is a hydrogen atom;

when $R^{23}$ represents a hydrogen atom, at least one of $R^{22}$ or $R^{24}$ represents a substituent;

$R^{25}$ represents a hydrogen atom, an oxygen atom, or a substituent;

$R^{22}$ and $R^{23}$, or $R^{23}$ and $R^{24}$ may be bonded together to form a ring with an oxygen atom and a carbon atom to which these Rs are bonded;

$R^{25}$ and $R^{26}$, or $R^{26}$ and $R^{27}$ may be bonded together to form a ring structure with carbon atoms to which these Rs are bonded;

X represents an oxygen atom or —CH$_2$—; and a dashed line may represent a double bond.

Herein, the compound represented by the formula (1) is also referred to as Compound (1).

In the present invention, in the formula (1), either one of the carbon atom to which $R^{21}$ is bonded or the carbon atom to which $R^{23}$ is bonded preferably reacts with an aldehyde. Compound (1) preferably does not substantially produce a compound represented by the following formula (2) by the reaction with an aldehyde.

[Chem. 2]

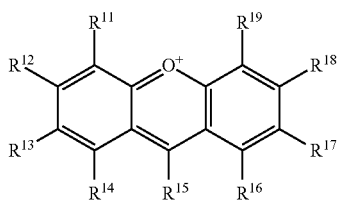

(2)

wherein $R^{11}$, $R^{12}$, $R^{13}$, $R^{14}$, $R^{15}$, $R^{16}$, $R^{17}$, $R^{18}$, and $R^{19}$ each independently represent a hydrogen atom or a substituent; $R^{11}$ and $R^{12}$, $R^{12}$ and $R^{13}$ and $R^{14}$ may be bonded together to form a ring structure with carbon atoms to which these Rs are bonded; and $R^{16}$ and $R^{17}$, $R^{17}$ and $R^{18}$, or $R^{18}$ and $R^{19}$ may be bonded together to form a ring structure with carbon atoms to which these Rs are bonded.

Herein, the compound represented by the formula (2) is also referred to as Compound (2).

In an exemplary embodiment of the present invention, in the formula (1), preferably, both positions adjacent (ortho) to a hydrogen atom bonded to the benzene ring are not occupied by hydroxyl groups.

In another exemplary embodiment of the present invention, in the formula (1), preferably, one position adjacent (ortho) to a hydrogen atom bonded to the benzene ring is occupied by a hydroxyl group, and at least one sterically hindered substituent is bonded to the benzene ring; and more preferably, a position adjacent (ortho) to the hydroxyl group is a sterically hindered substituent.

In an exemplary embodiment of the present invention, in the formula (1), preferably, $R^{21}$ represents a hydrogen atom, and $R^{22}$ and $R^{23}$ each independently represents a substituent. In another exemplary embodiment, in the formula (1), preferably, $R^{23}$ represents a hydrogen atom, and $R^{22}$ and $R^{24}$ each independently represent a substituent.

In still another exemplary embodiment, in the formula (1), preferably, $R^{21}$ represents a hydrogen atom; $R^{22}$ represents a hydrogen atom; and $R^{23}$ represents a sterically hindered substituent. In still another exemplary embodiment, in the formula (1), preferably, $R^{23}$ represents a hydrogen atom; $R^{21}$ represents a sterically hindered substituent; $R^{22}$ represents a hydrogen atom; and $R^{24}$ represents a substituent. In still yet another exemplary embodiment, in the formula (1), preferably, $R^{23}$ represents a hydrogen atom; $OR^{22}$ represents a sterically hindered substituent; and $R^{24}$ represents a hydrogen atom.

In the present invention, the sterically hindered substituent is preferably a C6-C30 organic group having a ring structure or a C10-C30 organic group having a linear or branched structure.

In the present invention, the substituent is preferably a hydroxyl group, a C1-C50 organic group, an amino group, a thiol group, a nitro group, or a halogen atom. The substituent is more preferably a hydroxyl group or a C1-C50 organic group.

The browning-inhibiting composition of the present invention is suitably used to inhibit browning in a polyphenol-containing composition. The polyphenol-containing composition is preferably a food or drink product containing polyphenols. The polyphenols are preferably catechins. The polyphenol-containing composition is preferably a green tea beverage.

The method for inhibiting browning in a polyphenol-containing composition of the present invention includes mixing the compound represented by the formula (1) with the polyphenol-containing composition. In the browning-inhibiting method of the present invention, the polyphenol-containing composition is preferably a food or drink product containing polyphenols. The polyphenols are preferably catechins. The polyphenol-containing composition is preferably a green tea beverage.

The method for producing a food or drink product of the present invention includes mixing the compound represented by the formula (1) with a food or drink product containing polyphenols.

In the production method of the present invention, the amount of the compound represented by the formula (1) is preferably 0.001 to 10% by mass relative to the food or drink product. The polyphenols are preferably catechins. In the production method of the present invention, the food or drink product containing polyphenols is preferably a green tea beverage.

The food or drink product of the present invention contains the compound represented by the formula (1).

The amount of the compound represented by the formula (1) is preferably 0.001 to 10% by mass relative to the food or drink product. The food or drink product of the present invention is preferably a green tea beverage.

After the green tea beverage is stored at room temperature for nine months, the percentage change in the area under an absorbance spectrum measured with light having a wavelength of 400 to 600 nm or in absorbance measured with light having a wavelength of 487 nm is preferably less than 150%.

The method for suppressing reduction of polyphenols in a polyphenol-containing composition of the present invention includes mixing the polyphenol-containing composition with the compound represented by the formula (1).

A method for suppressing production of the compound represented by the formula (2) in a polyphenol-containing composition of the present invention includes mixing the polyphenol-containing composition with the compound represented by the formula (1).

The aldehyde-scavenging composition of the present invention includes the compound represented by the formula (1).

In the aldehyde-scavenging composition of the present invention, in the formula (1), preferably, either one of the carbon atom to which $R^{21}$ is bonded or the carbon atom to which $R^{23}$ is bonded reacts with an aldehyde. Compound (1) preferably does not substantially produce the compound represented by the formula (2) by the reaction with an aldehyde.

The deodorizing composition of the present invention includes the aldehyde-scavenging composition of the present invention.

The deodorizing composition of the present invention is preferably for eliminating aldehyde-derived odors.

The method for screening for a compound having a browning-inhibiting effect on a polyphenol-containing composition of the present invention includes preparing a sample solution containing a polyphenol, an aldehyde, and a candidate compound; and determining the browning-inhibiting effect of the candidate compound, using as an indicator, the production of a compound represented by the formula (2) in the sample solution.

In the screening method of the present invention, preferably, the production of the compound represented by the formula (2) is detected by measuring an absorbance spectrum of the sample solution with light having a wavelength of 400 to 600 nm and determining the production based on the amount of change in the area under the absorbance spectrum; or by measuring absorbance of the sample solution with light having a wavelength of 487 nm and determining the production based on the amount of change in the absorbance.

More preferably, the production of the compound represented by the formula (2) is detected by measuring absorbance of the sample solution with light having a wavelength of 487 nm and determining the production based on changes in the absorbance.

The present invention also encompasses the following uses and the like.

Use of the compound represented by the formula (1) for inhibiting browning.

Use of the compound represented by the formula (1) for scavenging aldehydes.

Use of the compound represented by the formula (1) for eliminating odors.

An aldehyde-scavenging method including contacting the compound represented by the formula (1) with an aldehyde-containing gas or liquid.

A deodorizing method including contacting the compound represented by the formula (1) with an aldehyde-containing gas or liquid.

Advantageous Effects of Invention

The present invention provides, for example, a browning-inhibiting composition and a browning-inhibiting method, which are capable of inhibiting browning in a polyphenol-containing composition such as a green tea beverage. The present invention also provides a polyphenol-containing composition (such as a green tea beverage) that is less subject to browning even after long-term storage, a method for producing the same, and a method for inhibiting browning in a polyphenol-containing composition. The present invention also provides an aldehyde-scavenging composition.

DESCRIPTION OF EMBODIMENTS

Figure 1:
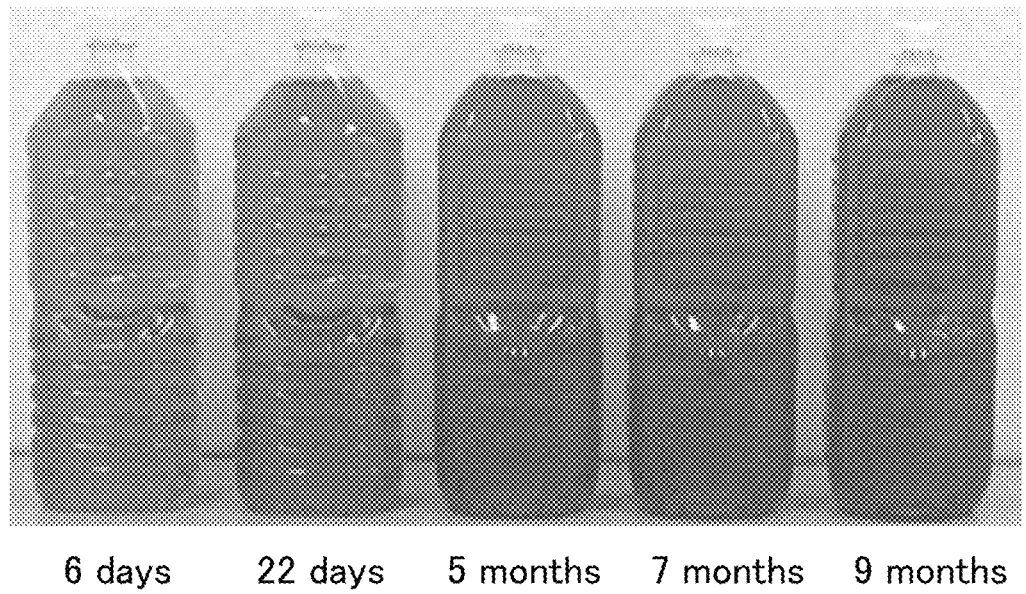
FIG. 1 is a picture showing the appearance of PET-bottled green tea beverages individually stored for 6 days, 22 days, 5 months, 7 months, and 9 months at room temperature.

The browning-inhibiting composition of the present invention contains a compound represented by the following formula (1):

[Chem. 3]

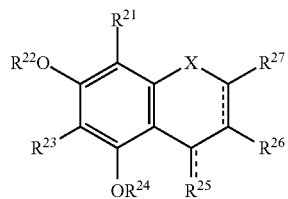

(1)

wherein $R^{21}$, $R^{22}$, $R^{23}$, $R^{24}$, $R^{26}$ and $R^{27}$ each independently represent a hydrogen atom or a substituent, and at least one of $R^{21}$ or $R^{23}$ is a hydrogen atom;

when $R^{23}$ represents a hydrogen atom, at least one of $R^{22}$ or $R^{24}$ represents a substituent;

$R^{25}$ represents a hydrogen atom, an oxygen atom, or a substituent;

$R^{22}$ and $R^{23}$, or $R^{23}$ and $R^{24}$ may be bonded together to form a ring with an oxygen atom and a carbon atom to which these Rs are bonded;

$R^{25}$ and $R^{26}$, or $R^{26}$ and $R^{27}$ may be bonded together to form a ring structure with carbon atoms to which these Rs are bonded; X represents an oxygen atom or —$CH_2$—; and a dashed line may represent a double bond.

Herein, a benzene ring to which $R^{21}$ and $R^{23}$ are bonded in the formula (1) is also referred to as a benzene ring A.

The browning-inhibiting composition of the present invention contains Compound (1) as an active ingredient.

In the formula (1), $R^{21}$ and $R^{23}$ each independently represent a hydrogen atom or a substituent. At least one of $R^{21}$ or $R^{23}$ is a hydrogen atom. That "at least one of $R^{21}$ or $R^{23}$ is a hydrogen atom" means that $R^{21}$ and $R^{23}$ are hydrogen atoms, or $R^{21}$ or $R^{23}$ is a hydrogen atom.

In the benzene ring A, at least one position adjacent (ortho) to the carbon atom to which $R^{21}$ is bonded is not occupied by a hydroxyl group. $R^{22}$ and $R^{24}$ each independently represent a hydrogen atom or a substituent. When $R^{23}$ represents a hydrogen atom, at least one of $R^{22}$ or $R^{24}$ ($R^{22}$ and/or $R^{24}$) represents a substituent.

As described above, in Compound (1), at least one position adjacent (ortho) to a hydrogen atom bonded to the benzene ring A is not occupied by a hydroxyl group.

Compound (1) in the present invention reacts with an aldehyde. Preferably, Compound (1) reacts with an aldehyde in a solution of pH 5 to 9, for example. In an embodiment, it is also preferred that Compound (1) reacts with an aldehyde in a solution of pH 6 to 6.5. In Compound (1), among carbon atoms constituting the benzene ring A, a carbon atom bonded to a hydrogen atom reacts with an aldehyde. This reaction is preferably a nucleophilic addition of an aldehyde to a carbonyl carbon. The number of positions at which the benzene ring A may react with an aldehyde (i.e., the number of carbon atoms each bonded to a hydrogen atom) is one when one of $R^{21}$ or $R^{23}$ is a hydrogen atom, and is two when $R^{21}$ and $R^{23}$ are hydrogen atoms. The number of positions at which the benzene ring A may react with an aldehyde is preferably one. The number of hydrogen atoms bonded to the benzene ring A is one or two, preferably one. In Compound (1), usually, at least one of the carbon atom to which $R^{21}$ is bonded or the carbon atom to which $R^{23}$ is bonded reacts with an aldehyde. Preferably, the carbon atom to which $R^{21}$ is bonded or the carbon atom to which $R^{23}$ is bonded reacts with an aldehyde.

Compound (1) in the present invention usually does not substantially produce a compound represented by the following formula (2) (Compound (2)) by the reaction with an aldehyde. That "does not substantially produce Compound (2) by the reaction with an aldehyde" means that the reaction of Compound (1) with an aldehyde does not produce Compound (2) or that even if Compound (2) is produced, the amount of production is so small that browning does not substantially occur.

The browning-inhibiting composition of the present invention usually does not contain Compound (2).

[Chem. 4]

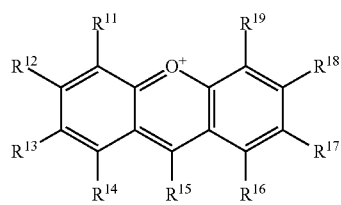

(2)

wherein $R^{11}$, $R^{12}$, $R^{13}$, $R^{14}$, $R^{15}$, $R^{16}$, $R^{17}$, $R^{18}$, and $R^{19}$ each independently represent a hydrogen atom or a substituent; $R^{11}$ and $R^{12}$, $R^{12}$ and $R^{13}$, or $R^{13}$ and $R^{14}$ may be bonded together to form a ring structure with carbon atoms to which these Rs are bonded; and $R^{16}$ and $R^{17}$, $R^{17}$ and $R^{18}$, or $R^{18}$ and $R^{19}$ may be bonded together to form a ring structure with carbon atoms to which these Rs are bonded.

Compound (2) exhibits yellowish brown to reddish brown due to a xanthylium structure represented by the formula (2). The xanthylium structure in Compound (2) has an absorption maximum around 440 nm near weak acidity (around pH 5), and an absorption maximum around 486 to 487 nm at a pH of 6.0 to 8.9 (NE Es-Safi et al., Food Chem 88 (2004), pp. 367-372). Thus, browning proceeds by the production of Compound (2).

In one example, a reaction in which Compound (2) is produced is as follows. Compound (2) is usually produced by reactions of polyphenols such as catechins with aldehydes. The following reaction scheme is an exemplary reaction in which an exemplary compound of Compound (2) is produced in a green tea beverage. The following reaction scheme shows an exemplary reaction between epicatechin (EC) as an exemplary catechin contained in a green tea beverage and an aldehyde (R-CHO).

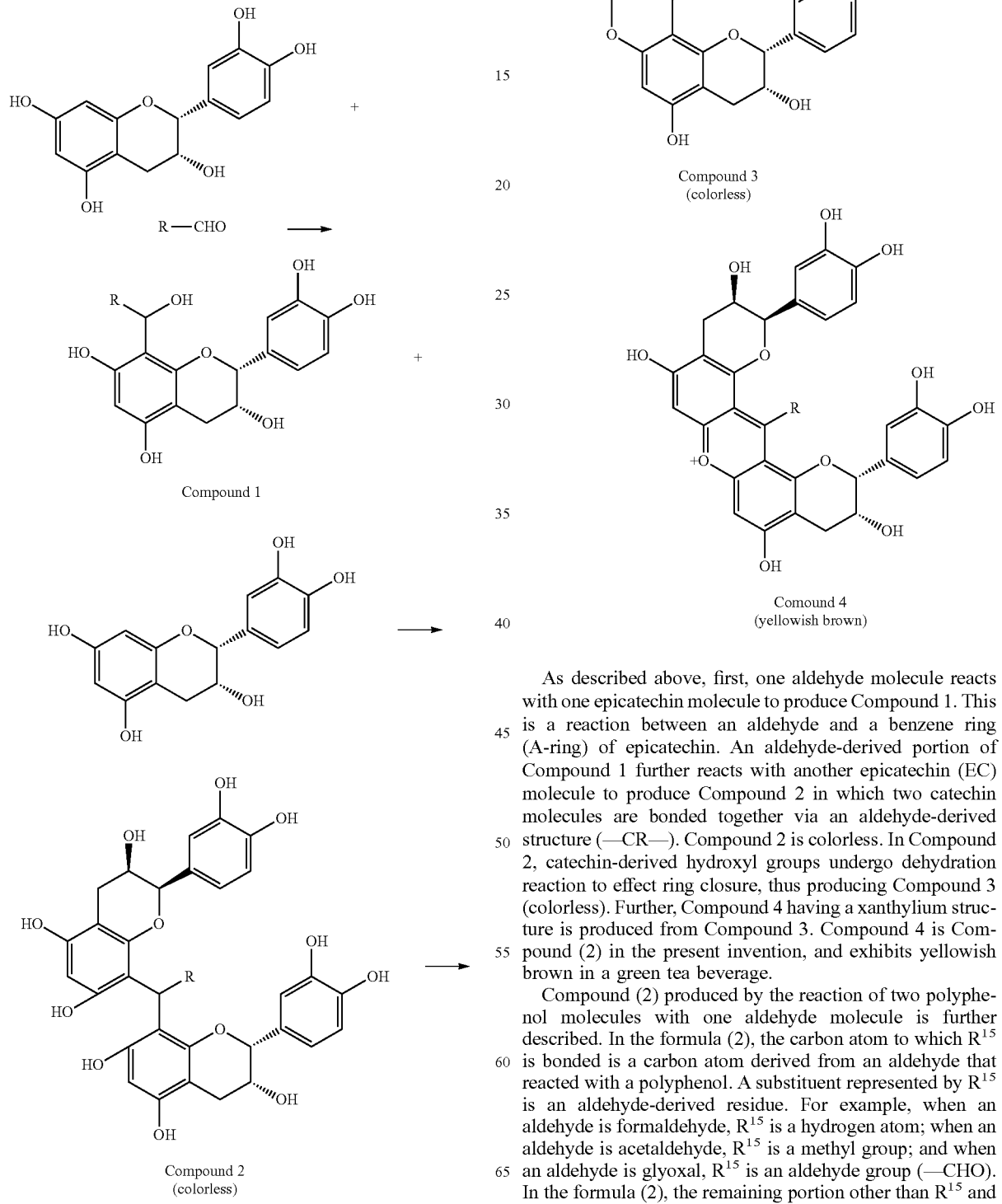

As described above, first, one aldehyde molecule reacts with one epicatechin molecule to produce Compound 1. This is a reaction between an aldehyde and a benzene ring (A-ring) of epicatechin. An aldehyde-derived portion of Compound 1 further reacts with another epicatechin (EC) molecule to produce Compound 2 in which two catechin molecules are bonded together via an aldehyde-derived structure (—CR—). Compound 2 is colorless. In Compound 2, catechin-derived hydroxyl groups undergo dehydration reaction to effect ring closure, thus producing Compound 3 (colorless). Further, Compound 4 having a xanthylium structure is produced from Compound 3. Compound 4 is Compound (2) in the present invention, and exhibits yellowish brown in a green tea beverage.

Compound (2) produced by the reaction of two polyphenol molecules with one aldehyde molecule is further described. In the formula (2), the carbon atom to which $R^{15}$ is bonded is a carbon atom derived from an aldehyde that reacted with a polyphenol. A substituent represented by $R^{15}$ is an aldehyde-derived residue. For example, when an aldehyde is formaldehyde, $R^{15}$ is a hydrogen atom; when an aldehyde is acetaldehyde, $R^{15}$ is a methyl group; and when an aldehyde is glyoxal, $R^{15}$ is an aldehyde group (—CHO). In the formula (2), the remaining portion other than $R^{15}$ and the carbon atom to which $R^{15}$ is bonded is derived from a polyphenol that reacted with an aldehyde. For example, when Compound (2) is Compound 4 produced by a reaction of one aldehyde molecule with two epicatechin molecules, $R^{11}$ and $R^{19}$ are hydrogen atoms, and $R^{12}$ and $R^{18}$ are hydroxyl groups.

A compound produced by a reaction of one molecule of Compound (1) with one aldehyde (R—CHO) molecule has a structure in which a hydrogen atom of the benzene ring A is replaced by an aldehyde. An aldehyde-derived carbon atom in this compound may further react with the benzene ring A of another molecule of Compound (1). In this case, a dimer of Compound (1) is generated in which two molecules of Compound (1) are bonded to each other via an aldehyde-derived structure (—CR—). Here, in the benzene ring A of Compound (1) forming a dimer, when positions adjacent (ortho) to a binding position to an aldehyde (i.e., a carbon atom to which $R^{21}$ or $R^{23}$ is bonded in the formula (1)) are both occupied by hydroxyl groups, condensation of the hydroxyl groups may occur in the dimer, producing Compound (2). In the present invention, at least one position adjacent (ortho) to a hydrogen atom boned to the benzene ring A (i.e., a position at which the reaction with an aldehyde occurs) is not occupied by a hydroxyl group. This substantially prevents production of Compound (2) even when Compound (1) reacts with an aldehyde. Thus, Compound (1) can scavenge aldehydes and inhibit browning. Scavenging aldehydes by Compound (1) reduces reactions between polyphenols and aldehydes, and the production of Compound (2) is thus suppressed. Compound (1) in the present invention is effective as an active ingredient of the browning-inhibiting composition.

Compound (1) in the present invention may have one or more heterocyclic (C6-C3) structures with the benzene ring A represented by the formula (1) in one molecule. Preferably, Compound (1) has one such heterocyclic structure. In addition, preferably, Compound (1) does not have a benzene ring structure in which, among carbon atoms constituting the benzene ring, both positions adjacent (ortho) to a carbon atom bonded to a hydrogen atom are occupied by hydroxyl groups.

In the present invention, Compound (1) does not substantially produce Compound (2) by the reaction with an aldehyde, so that it can scavenge aldehydes and suppress production of Compound (2) to inhibit browning.

Compound (1) in the present invention preferably is colorless at a pH of 2 to 13. Such a compound can exert a better browning-inhibiting effect.

That "Compound (1) does not substantially produce Compound (2) by the reaction with an aldehyde" can be confirmed, for example, by the fact that when an aldehyde is added to a solution of Compound (1), the solution does not substantially change in the visible absorption spectrum at 400 to 600 nm before and after addition.

The substituent in the formula (1) and the formula (2) is not particularly limited, but is preferably a hydroxyl group, a C1-C50 organic group, an amino group (—$NH_2$), a thiol group (—SH), a nitro group (—$NO_2$), or a halogen atom. In particular, the substituent is more preferably a hydroxyl group or a C1-C50 organic group. In an embodiment, the carbon number of the organic group is more preferably 1 to 30, still more preferably 1 to 20, particularly preferably 1 to 15. The organic group is a carbon atom-containing group, and may include other atoms such as hydrogen, oxygen, nitrogen, sulfur, halogen, and phosphorus atoms, in addition to the carbon atom. The organic group in the present invention is more preferably an organic group consisting of carbon, hydrogen, and oxygen atoms, or an organic group consisting of carbon and hydrogen atoms.

Examples of the C1-C50 organic group includes groups such as alkyl, alkenyl, alkynyl, alkoxy, alkenyloxy, alkylcarbonyl, alkenylcarbonyl, alkylthio, alkylamino, aryl, arylalkyl, aryloxy, arylcarbonyl, arylthio, arylamino, arylalkylthio, heterocyclic, heterocyclic-oxy, cyano, and carboxyl groups. These groups may be substituted with one or more substituents. When these groups are substituted with substituents, the carbon number including these substituents is preferably within the above range. That "these groups are substituted with substituents" means that hydrogen atoms in these organic groups are replaced with substituents. These organic groups may each have a linear, branched, or cyclic structure.

When Compound (1) in the present invention has geometric isomers, the present invention encompasses all such geometric isomers. In addition, when Compound (1) contains one or more chiral carbon atoms, the present invention also encompasses compounds in which each chiral carbon atom has an R configuration, compounds in which each chiral carbon atom has an S configuration, and compounds in which chiral carbons atoms having R and S configurations are combined. The present invention also encompasses racemic compounds, racemic mixtures, single enantiomers, and diastereomer mixtures of such compounds.

Compound (1) is described in more detail.

In Compound (1), the larger the number of oxygen atoms bonded to the benzene ring A, the higher the reactivity of the benzene ring A with an aldehyde. At least two oxygen atoms are bonded to the benzene ring A via $OR^{22}$ and $OR^{24}$. In an embodiment, the number of oxygen atoms bonded to the benzene ring A is preferably three or four. Such a compound is preferably, for example, a compound in which X is an oxygen atom, and/or $R^{21}$ or $R^{23}$ is a substituent represented by $OR^{a1}$ ($R^{a1}$ represents a hydrogen atom or a substituent). For example, when $R^{21}$ is a hydrogen atom, preferably, X is an oxygen atom, and/or $R^{23}$ is a substituent represented by $OR^{a1}$ ($R^{a1}$ is as defined above). In another embodiment, when $R^{23}$ is a hydrogen atom, preferably, x is an oxygen atom, and/or $R^{21}$ is a substituent represented by $OR^{a1}$ ($R^{a1}$ is as defined above). Examples of substituents for $R^{a1}$ include those mentioned above.

In one preferred exemplary embodiment of the formula (1), preferably, both positions adjacent (ortho) to a hydrogen atom bonded to the benzene ring (benzene ring A) are not occupied by hydroxyl groups. As described above, in Compound (1), among carbon atoms constituting the benzene ring A, a carbon atom bonded to a hydrogen atom reacts with an aldehyde. Since ortho positions to a position at which the reaction with an aldehyde occurs are not occupied by hydroxyl groups, usually, Compound (2) is not produced when two molecules of Compound (1) reacts with one aldehyde molecule. Thus, Compound (1) can exhibit an excellent browning-inhibiting effect. In an embodiment, for example, when $R^{21}$ is a hydrogen atom, $R^{22}$ is preferably a substituent. When $R^{23}$ is a hydrogen atom, $R^{22}$ and $R^{24}$ are preferably each independently a substituent.

In the formula (1), when one position adjacent (ortho) to a hydrogen atom bonded to the benzene ring (benzene ring A) is occupied by a hydroxyl group, preferably, at least one sterically hindered substituent is bonded to the benzene ring, and more preferably, a position adjacent (ortho) to the hydroxyl group is occupied by a sterically hindered substituent. Compound (1) having such a structure exhibits a better browning-inhibiting effect.

The sterically hindered substituent means a group that reduces reactivity of a hydroxyl group with another hydroxyl group by sterical hindrance when a carbon atom constituting the benzene ring A reacts with an aldehyde. Specifically, a hydroxyl group bonded to a carbon atom at a position adjacent (ortho) to a position at which the reaction occurred with the aldehyde is rendered less reactive with another hydroxyl group, due to sterical hindrance of the sterically hindered substituent.

As described above, the reaction of Compound (1) with an aldehyde (R-CHO) may generate a dimer of Compound (1) in which two molecules of Compound (1) are bonded to each other via an aldehyde-derived structure (—CR—). Here, even when both benzene rings A of the two molecules of Compound (1) forming a dimer each contain a hydroxyl group at one position ortho to a position at which the reaction with an aldehyde occurs, if at least one sterically hindered substituent is bonded to these benzene rings A, condensation of two hydroxyl groups derived from Compound (1) is inhibited in the dimer. In addition, when one position adjacent (ortho) to a hydrogen atom bonded to each benzene ring A is occupied by a hydroxyl group, if a position adjacent (ortho) to the hydroxyl group is occupied by a sterically hindered substituent, condensation of two hydroxyl groups derived from Compounds (1) is more sufficiently inhibited in the dimer. As a result, usually, Compound (2) is not produced, and browning is inhibited.

For example, when $R^{21}$ is a hydrogen atom and $R^{22}$ is a hydrogen atom, preferably, at least one of $R^{23}$ or $OR^{24}$ is a sterically hindered substituent, and more preferably $R^{23}$ is a sterically hindered substituent.

The sterically hindered substituent is not particularly limited as long as it is a group that reduces reactivity of the hydroxyl group. Preferably, the sterically hindered substituent is a C6-C30 organic group having a ring structure or a C10-C30 organic group having a linear or branched structure. More preferably, the sterically hindered substituent is a C6-C30 organic group having a ring structure. The ring structure is preferably a six-membered ring. The carbon number of the C6-C30 organic group having a ring structure is preferably 6 to 20, more preferably 6 to 15. The C6-C30 organic group having a ring structure may be a gallate group or a sugar (sugar residue). The sugar may be a monosaccharide or polysaccharide (preferably, a disaccharide, trisaccharide, tetrasaccharide, or pentasaccharide, more preferably a disaccharide).

In Compound (1), $R^{21}$ or $R^{23}$ is preferably a hydrogen atom. Such a compound is preferred because of its high browning-inhibiting effect. A compound represented by the formula (1) in which $R^{21}$ is a hydrogen atom and $R^{23}$ is a substituent, or a compound represented by the formula (1) in which $R^{23}$ is a hydrogen atom and $R^{21}$ is a substituent is preferred as Compound (1) in the present invention.

Compound (1) is preferably any of the following Compounds (i) to (v), for example.

In the formula (1),
(i) a compound in which $R^{21}$ represents a hydrogen atom, and $R^{22}$ and $R^{23}$ each independently represents a substituent;
(ii) a compound in which $R^{23}$ represents a hydrogen atom, and $R^{22}$ and $R^{24}$ each independently represent a substituent;
(iii) a compound in which $R^{21}$ represents a hydrogen atom, $R^{22}$ represents a hydrogen atom, and $R^{23}$ represents a sterically hindered substituent;
(iv) a compound in which $R^{23}$ represents a hydrogen atom, $R^{21}$ represents a sterically hindered substituent, $R^{22}$ represents a hydrogen atom, and $R^{24}$ represents a substituent; and
(v) a compound in which $R^{23}$ represents a hydrogen atom, $OR^{22}$ represents a sterically hindered substituent, and $R^{24}$ represents a hydrogen atom.

In Compounds (i) and (ii), both ortho positions to the position at which the reaction occurs with an aldehyde are not occupied by hydroxyl groups, so that usually the reaction of Compound (1) with an aldehyde does not produce Compound (2). In Compound (ii), it is more preferred that $R^{21}$ is a hydrogen atom. In Compounds (iii), (iv), and (v), usually, the sterically hindered substituent suppresses production of Compound (2). Such Compound (1) can exert an excellent browning-inhibiting effect. The sterically hindered substituent and preferred embodiments thereof are as described above. Among Compounds (iii), (iv), and (v), Compounds (iii) and (iv) are more preferred.

One of preferred examples of substituents in Compounds (i) to (v) is a hydroxyl group or a C1-C10 (preferably C1-C8, more preferably C1-C6) organic group.

When $R^{22}$ and $R^{23}$, or $R^{23}$ and $R^{24}$ are bonded together to form a ring with an oxygen atom and a carbon atom to which these Rs are bonded, the ring is preferably a six-membered ring, and the ring may be substituted with a substituent.

In the formula (1), $R^{25}$ is preferably an oxygen atom or a substituent.

$R^{26}$ and $R^{27}$ each independently represent a hydrogen atom or a substituent. $R^{25}$ and $R^{26}$, or $R^{26}$ and $R^{27}$ may be bonded together to form a ring structure with carbon atoms to which these Rs are bonded.

Examples of preferred substituents for $R^{25}$, $R^{26}$ and $R^{27}$ include C1-C15 organic groups. Aryl groups and the sugar residues mentioned above are preferred as the organic groups. In an embodiment, preferably, any one of $R^{25}$, $R^{26}$ or $R^{27}$ is an aryl group. In one preferred exemplary embodiment, $R^{25}$ is an oxygen atom or an aryl group, and when $R^{25}$ is an oxygen atom, $R^{26}$ or $R^{27}$ is an aryl group. The aryl group may be substituted with one or more substituents. For example, a C6-C15 aryl group optionally substituted with one or more substituents is preferred.

Among Compounds (i) to (v), a compound in which $R^{25}$, $R^{26}$, and $R^{27}$ are as described above is one preferred exemplary embodiment of Compound (1) in the present invention.

Examples of Compound (1) in the present invention include compounds represented by the following formulas (A-1), (A-2), (A-3), (A-4), and (A-5), baicalin, baicalin glycosides (for example, a compound containing one to three glucose molecules bonded to a sugar moiety of baicalin), chafuroside A, icariin, and scutellarin. Each of these compounds is preferred as Compound (1) in the present invention.

[Chem. 6]

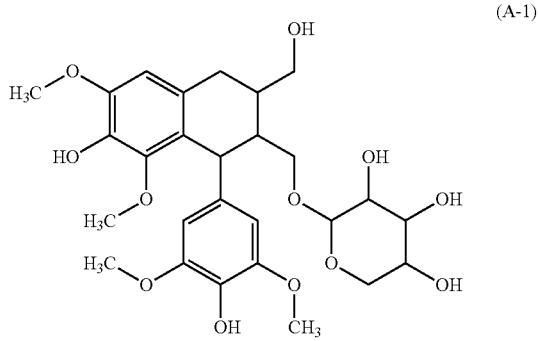

(A-1)

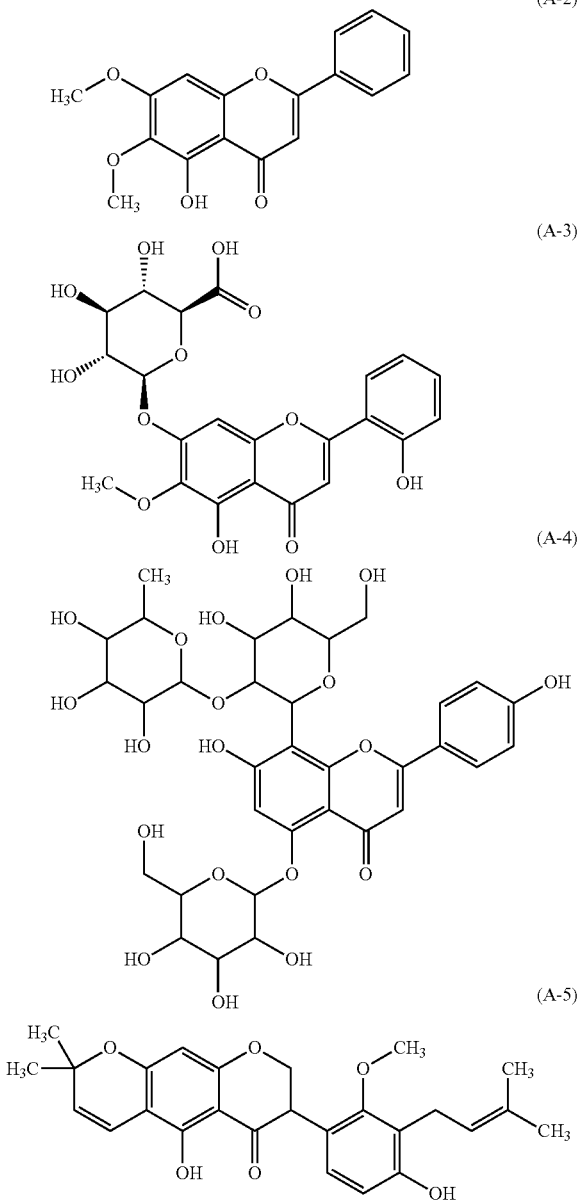

Examples of Compound (1) in the present invention also include compounds represented by the following formulas (A-6), (A-7), (A-8), and (A-9). The compounds represented by the formulas (A-6) to (A-9) are also examples of Compound (1).

[Chem. 7]

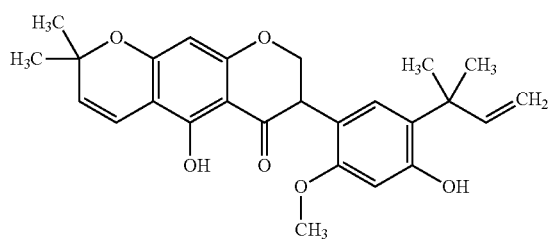

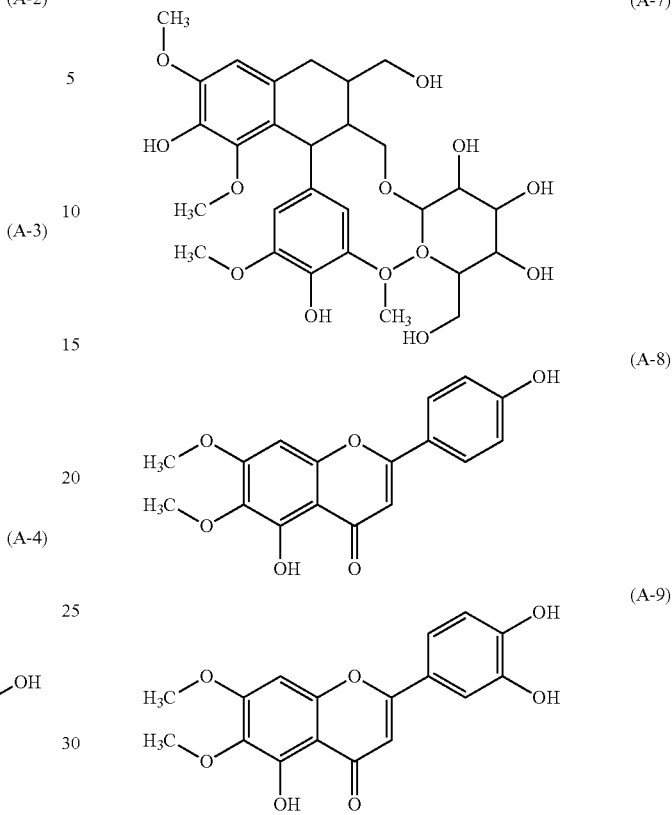

Compound (1) in the present invention preferably has a solubility of 0.01% by mass or more in water. The solubility is more preferably 0.01 to 50% by mass, still more preferably 0.1 to 40% by mass, particularly preferably 0.5 to 30% by mass, most preferably 1 to 20% by mass. Preferably, the solubility in water is in the above ranges at 20° C. Compound (1) having a solubility in the above ranges in water can exert a sufficient browning-inhibiting effect on various food or drink products.

The browning-inhibiting composition of the present invention contains one or more Compounds (1).

Compound (1) in the present invention may be produced by any method, such as a known organic synthesis method. Alternatively, a commercial product can be used. Compound (1) can also be isolated from natural sources by a known method.

In the present invention, Compound (1) may be directly used as a browning-inhibiting composition (or a browning inhibitor). The browning-inhibiting composition of the present invention may contain additional components other than Compound (1), if desired, as long as the effect of the present invention is not impaired. Additional components may be known components. Examples of the other components include additives. For example, in the case of adding the browning-inhibiting composition to a food or drink product, the browning-inhibiting composition may further contain known additives commonly used in food or drink products. Examples of the additives for food or drink products include bulking agents, antioxidants, pH regulators, colorants, essence, flavoring substances, surfactants (emulsifiers), solubilizers, preservatives, sugars, sweeteners, acidulants, and vitamins. The browning-inhibiting composition of the present invention may be used in combination with other browning inhibitor(s).

The browning-inhibiting composition, the aldehyde-scavenging composition (described later), and the deodorizing composition (described later) of the present invention can be provided as agents as an example, but may be provided in any form. These agents can be provided directly as compositions, or can be provided as compositions containing these agents.

The form of the browning-inhibiting composition of the present invention is not particularly limited. For example, the browning-inhibiting composition may be in the form of powder, granules, paste, solid, or liquid.

The amount of Compound (1) in the browning-inhibiting composition of the present invention is not particularly limited, but in an embodiment, the amount is preferably 0.01 to 99.9% by mass, more preferably 1 to 50% by mass, for example.

Adding Compound (1) to a polyphenol-containing composition enables inhibition of browning in the polyphenol-containing composition. The browning-inhibiting composition of the present invention is suitably used to inhibit browning in a polyphenol-containing composition.

The method for inhibiting browning in a polyphenol-containing composition which includes mixing Compound (1) with the polyphenol-containing composition is also encompassed by the present invention.

In the present invention, the polyphenol-containing composition is preferably a polyphenol-containing food or drink product. Use of Compound (1) enables production of a food or drink product in which browning is inhibited. A method for producing a food or drink product which includes mixing Compound (1) with a food or drink product containing polyphenols is also encompassed by the present invention. Polyphenol-containing compositions, such as food and drink products, usually contain an aldehyde in a component of raw materials or the like, or an aldehyde is produced by time-dependent degradation or the like of the component. Compound (1) can inhibit browning by scavenging aldehydes. One or more Compounds (1) are used. The browning-inhibiting composition of the present invention is suitably used in the browning-inhibiting method, the method for producing a food or drink product, a food or drink product (described later), and the like. The food or drink product encompasses raw materials of the food or drink product.

Polyphenols in the present invention are those derived from plants or from processed products thereof. Here, a polyphenol refers to a phenol having at least two hydroxyl groups in the same benzene ring, and its glycoside is also one of polyphenols. Compound (1) in the present invention is usually not included in the polyphenols in the present invention. The polyphenols in the present invention are preferably compounds that produce Compound (2) by reactions with aldehydes. One of such polyphenols is a polyphenol having a benzene ring structure in which among carbon atoms constituting the benzene ring, both positions adjacent (ortho) to a carbon atom bonded to a hydrogen atom are occupied by hydroxyl groups.

Examples of such a polyphenol include flavonoids such as flavan-3-ols, flavones, isoflavones, flavonols, flavanons, flavanonols, and flavan-3,4-diols, and related compounds thereof. Examples of the related compounds of flavonoids include flavonoid glycoside.

Examples of polyphenols contained in tea beverages include flavan-3-ols and related compounds thereof, such as catechins including epicatechin, epicatechin gallate, epigallocatechin, epigallocatechin gallate, gallocatechin, gallocatechin gallate, catechin, and catechin gallate; and theaflavins including theaflavin, theaflavin gallate A, theaflavin gallate B, and theaflavin digallate.

The polyphenols in the present invention are preferably catechins. Compound (1) is particularly suitably used to inhibit browning in a catechin-containing composition.

The food or drink product containing polyphenols is not particularly limited. Examples include tea beverages such as green tea, buckwheat tea, barley tea, black tea, pu-erh tea, oolong tea, and Hojicha; fruit juices such as grape, apple, citrus fruit, and peach, and soft drinks containing fruit juices; beverages such as alcoholic beverages containing any of the above fruit juices or tea beverages; and soy products such as fermented soybean paste and soy milk. Examples of the alcoholic beverages containing any of the above fruit juices or tea beverages include alcoholic beverages such as beer, shochu highball, liqueurs, and cocktails containing any of the above fruit juices or tea beverages. In particular, Compound (1) is suitably used to inhibit browning in beverages containing polyphenols, and is more suitable to tea beverages, still more suitable to green tea beverages.

Tea beverages can be obtained by extracting various kinds of tea products mainly using leaves and twigs of tea tree (scientific name: Camellia sinensis) (e.g., black tea, oolong tea, pu-erh tea, and green tea) or products obtained by blending such tea with various kinds of plant materials (e.g., brown rice, wheats, and barleys), with hot water, warm water, cold water, ethanol, water-containing ethanol, or the like. Browning in extract occurs in any of the above tea beverages, but the present invention is particularly useful in green tea beverages whose changes in color due to browning are noticeable. The browning-inhibiting composition and the browning-inhibiting method of the present invention are particularly suitably used to inhibit browning in green tea beverages. The method for producing a food or drink product of the present invention is particularly suitable for production of green tea beverages. The green tea beverage in the present invention is not particularly limited as long as it is a tea beverage containing green tea extract.

In the case of mixing Compound (1) with a food or drink product containing polyphenols, Compound (1) may be mixed at any time. For example, Compound (1) may be mixed during or of ter production of the food or drink product. The method for mixing Compound (1) with the food or drink product is also not particularly limited.

The following describes an example of the method for producing a tea beverage.

Raw materials (tea leaves or the like) are extracted with warm water or hot water, and then tea dregs or fine particles are removed by filtration or the like. Then, the extract is diluted to an adequate concentration, and ascorbic acid or sodium ascorbate is added to the diluted solution. In addition to ascorbic acid or sodium ascorbate, preferably, a pH regulator such as soda (sodium hydrogen carbonate) is added to the diluted solution. The diluted solution of the tea extract containing ascorbic acid or sodium ascorbate is referred to as a preparation. The preparation may be prepared by adding ascorbic acid or sodium ascorbate to the extract before diluting the extract. The preparation is preferably heat-sterilized. Sterilization by ultra-high temperature method (UHT method) is also preferred. In the case of using a PET bottle or the like as a container, preferably, the preparation is heat-sterilized before being packed in the container. When the preparation is packed in a can or the like as a container, preferably, the container containing the preparation is heat-sterilized. When the preparation is packed in a container, air in the head space of the container can be purged with nitrogen gas.

For example, in the case of mixing Compound (1) in the production of tea beverages, preferably, Compound (1) is mixed before the tea beverages are heat-sterilized. Compound (1) may be mixed in advance with warm water or hot water to be used for extraction, or may be mixed with an extract or a preparation. Yet, mixing with a preparation is preferred.

In one preferred exemplary embodiment of the present invention, the method for producing a green tea beverage includes the following steps: extracting raw materials including tea leaves of green tea with warm water or hot water (preferably at 65° C. to 90° C.); filtering the extract; diluting the filtered extract with water; mixing the diluted solution with ascorbic acid or sodium ascorbate (preferably, 0.1 to 1 g/L, more preferably 0.3 to 0.5 g/L), soda (preferably 0.1 to 1 g/L, more preferably 0.3 to 0.4 g/L), and Compound (1) to obtain a preparation; and heat-sterilizing (preferably at 100° C. to 135° C. for 10 to 120 seconds) the preparation. The method including the above steps is also preferred as a method for inhibiting browning in a green tea beverage. In addition, when the method includes packing the heat-sterilized green tea beverage in a container such as a PET bottle, the method can produce a container-packed green tea beverage.

Compound (1) is also suitably used in concentrated tea extract. In the case of concentrated tea extract, the tea extract may be mixed with Compound (1) before or after concentration. Also, powder (powdered tea) can be produced by drying and powdering the concentrated tea extract. Adding Compound (1) to tea extract can inhibit browning from proceeding in the concentrated tea extract or powder. The concentrated tea extract or powder, when diluted with water or the like, can be used as a beverage. The concentrated tea extract or powder can also be used in food or drink products other than tea beverages. The browning-inhibiting effect is also maintained in such food or drink products containing the concentrated tea extract.

In the case of mixing a polyphenol-containing composition (preferably, a food or drink product containing polyphenols) with Compound (1), the Compound (1) maybe used in any amount, preferably in an effective amount as appropriate. For example, the amount of Compound (1) is preferably 0.001 to 10% by mass, more preferably 0.01 to 1% by mass relative to the polyphenol-containing composition. When the amount is in above ranges, a favorable browning-inhibiting effect can be obtained. For example, when the polyphenol-containing composition is a tea beverage, the amount of Compound (1) to be used is preferably 0. 001 to 10% by mass, more preferably 0.01 to 1% by mass relative to the tea beverage.

Mixing Compound (1) with a polyphenol-containing green tea beverage or the like can provide a beverage suitable for a clear container such as a PET bottle. When using Compound (1), additionally, air in the head space of the beverage container may be purged with nitrogen gas, or other browning inhibitor(s) may be used in combination.

A food or drink product containing Compound (1) is also encompassed by the present invention. The food or drink product is not particularly limited, and examples include the food or drink products containing polyphenols mentioned above. Beverages are preferred, tea beverages are more preferred, and green tea beverages are still more preferred.

The beverage of the present invention may be one that can be consumed directly without being diluted. In addition, the beverage may be a powdered soft drink that is in the form of powder at the time of sale and that is consumed by being dissolved in water or like to an appropriate concentration at the time of drinking, or may be a concentrated beverage which is consumed by being diluted in water or the like.

The amount of Compound (1) is not particularly limited. Yet, for example, the amount of Compound (1) is preferably 0.001 to 10% by mass, more preferably 0.01 to 1% by mass in the food or drink product.

The food or drink product of the present invention is preferably a container-packed beverage. Examples of containers for container-packed beverages include molded containers mainly containing polyethylene terephthalate (PET bottles), metal cans, paper containers combined with metal foil or plastic films, and bottles. In particular, the present invention is useful for container-packed beverages in clear containers such as PET bottles or glass bottles.

After the green tea beverage of the present invention is stored at room temperature for nine months, the percentage change in the area under an absorbance spectrum measured with light having a wavelength of 400 to 600 nm or in absorbance of a sample solution measured with light having a wavelength of 487 nm is preferably less than 150%. The green tea beverage in which the percentage change in the area or the absorbance is less than 150% is preferred as a green tea beverage in which browning is inhibited. The "room temperature" is usually 1° C. to 30° C., preferably 15° C. to 25° C.

In an exemplary preferred embodiment of the present invention, a green tea beverage contains the compound represented by the formula (1) and catechins, wherein after the green tea beverage is stored at room temperature for nine months, the percentage change in the area under an absorbance spectrum measured with light having a wavelength of 400 to 600 nm or in absorbance measured with light having a wavelength of 487 nm is less than 150%. Such a green tea beverage is also encompassed by the present invention.

The percentage change in the area under the absorbance spectrum is determined from the following formula using the area under an absorbance spectrum (S0) at 400 to 600 nm of a green tea beverage before storage and the area under an absorbance spectrum (S1) at 400 to 600 nm of the green tea beverage after nine-month storage at room temperature.

Percentage change in area under absorbance spectrum (%)=100×(S1-S0)/S0

The percentage change in the area under the absorbance spectrum is preferably less than 50%.

The percentage change in the absorbance at a wavelength 487 nm is determined from the following formula using absorbance (A0) at 487 nm of a green tea beverage before storage and absorbance (A1) at 487 nm of the green tea beverage after nine-month storage at room temperature.

Percentage change (%) in absorbance at wavelength of 487 nm=100×(A1-A0)/A0

Percentage change in the absorbance at a wavelength of 487 nm is preferably less than 50%.

Compound (1) inhibits browning by scavenging aldehydes as described above. Thus, Compound (1) is useful as an active ingredient of an aldehyde-scavenging composition. The browning-inhibiting composition of the present invention can be used as an aldehyde-scavenging composition.

The aldehyde-scavenging composition of the present invention contains Compound (1). The aldehyde-scavenging composition of the present invention contains Compound (1) as an active ingredient. The aldehyde-scavenging composition contains one or more Compounds (1). Compound (1) and preferred embodiments thereof are the same as those of the browning-inhibiting composition. For example, in the formula (1), either one of the carbon atom to which $R^{21}$ is bonded or the carbon atom to which $R^{23}$ is bonded preferably reacts with an aldehyde. Compound (1) preferably does not substantially produce Compound (2) by the reaction with an aldehyde. In the present invention, Compound (1) may be directly used as an aldehyde-scavenging composition (or an aldehyde scavenger). The aldehyde-scavenging composition may contain additional components (other components) other than Compound (1), if desired, as long as the effect of the present invention is not impaired. Other components can be suitably selected according to the usage form or the like of the aldehyde-scavenging composition. Examples of other components include additives.

In an embodiment, for example, the amount of Compound (1) in the aldehyde-scavenging composition is preferably 0.01 to 99.9% by mass, more preferably 1 to 50% by mass.

The aldehyde-scavenging composition is suitably used, for example, to scavenge aldehydes in air or solutions. For example, the aldehyde-scavenging composition is allowed to contact with an aldehyde-containing gas or liquid, whereby aldehydes in the air or liquid can be scavenged. The aldehyde-scavenging composition is suitably used to eliminate aldehyde-derived odors. The aldehyde-scavenging composition can also be used to scavenge aldehydes in vivo or scavenging aldehydes which are causative substances of sick building syndrome.

The method for suppressing reduction of polyphenols in a polyphenol-containing composition of the present invention includes mixing the polyphenol-containing composition with Compound (1). Compound (1) and preferred embodiments thereof are as described above. One or more Compounds (1) are used.

Mixing the polyphenol-containing composition with Compound (1) inhibits reactions of polyphenols in the composition with aldehydes, thus suppressing reduction of polyphenols in the composition.

The amount of Compound (1) is not particularly limited, and may be suitably selected according to the polyphenol-containing composition, but the amount is preferably 0.001 to 10% by mass, more preferably 0.01 to 1% by mass, relative to the polyphenol-containing composition. For example, if the polyphenol-containing composition is a tea beverage, the amount of Compound (1) is preferably 0.001 to 10% by mass, more preferably 0.01 to 1% by mass, relative to the tea beverage.

The polyphenol-containing composition is preferably a food or drink product containing polyphenols. The composition is preferably a composition containing catechins, more preferably a tea beverage, still more preferably a green tea beverage. The method for suppressing reduction of polyphenols of the present invention is useful as a method for suppressing reduction of catechins in a green tea beverage.

For example, green tea beverages exhibit refreshing bitterness immediately after production, but after long-term storage, this refreshing bitterness decreases in some cases. One of the causes of changes in flavor is considered to reduction of catechins due to reactions with aldehydes during storage. The present invention can provide a green tea beverage that exhibits less reduction of catechins, less changes in flavor, and less browning even after long-term storage.

A method for suppressing production of the compound represented by the formula (2) in a polyphenol-containing composition of the present invention includes mixing the polyphenol-containing composition with Compound (1). As described above, use of Compound (1) can suppress production of Compound (2) in the polyphenol-containing composition.

Compound (1) and preferred embodiments thereof are as described above. One or more Compounds (1) are used.

The amount of Compound (1) is not particularly limited, and may be suitably selected according to the polyphenol-containing composition. Yet, the amount is preferably 0.001 to 10% by mass, more preferably 0.01 to 1% by mass, relative to the polyphenol-containing composition. For example, if the polyphenol-containing composition is a tea beverage, the amount of Compound (1) is preferably 0.001 to 10% by mass, more preferably 0.01 to 1% by mass, relative to the tea beverage.

The deodorizing composition of the present invention includes the aldehyde-scavenging composition of the present invention.

The deodorizing composition of the present invention can effectively reduce aldehyde-derived odors by scavenging aldehydes by Compound (1). Thus, the deodorizing composition of the present invention is suitably used as a deodorizing composition for eliminating aldehyde-derived odors. Compound (1) is suitably used as an active ingredient of the deodorizing composition.

Compound (1) and preferred embodiments thereof are as described above. For example, in the formula (1), either one of the carbon atom to which $R^{21}$ is bonded or the carbon atom to which $R^{23}$ is bonded preferably reacts with an aldehyde. Compound (1) preferably does not substantially produce Compound (2) by the reaction with an aldehyde. The deodorizing composition contains one or more Compounds (1).

The deodorizing composition of the present invention is effective against various kinds of odors such as body odors (armpit odor, foot odor, sweat odor, scalp odor, and the like), kitchen smell, smell in refrigerator, smell of food such as fish and vegetables, smell of cigarette smoke, smell of clothes, and smell of shoes. Thus, the deodorizing composition of the present invention can be used as a deodorizing composition or the like for bad breath, body odors, kitchen use, indoor use, daily use, in-vehicle use, or industrial use, for example.

In addition, since Compound (1) does not substantially produce Compound (2) by the reaction with an aldehyde, browning does not occur even when Compound (1) scavenges aldehydes which are odor components. Thus, the deodorizing composition of the present invention also achieves the effect that browning is less likely to occur in fabric products such as clothes and furniture even when the deodorizing composition is repeatedly used in the fabric products. Thus, the deodorizing composition of the present invention is suitably used as a deodorizing composition for fabric, for example.

In the present invention, the aldehyde-scavenging composition may be directly used as a deodorizing composition. Compound (1) can be directly used as a deodorizing composition (or a deodorant). The amount of Compound (1) in the deodorizing composition is not particularly limited. For example, in an embodiment, the amount is preferably 0.01 to 99.9% by mass, more preferably 1 to 50% by mass.

The deodorizing composition may contain additional components other than Compound (1). For example, the deodorizing composition may contain common additives as necessary, such as antioxidants, ultraviolet absorbers, antistatic agents, flame retardants, antiseptics, fungicides, insect repellents, pigments, colorant, and flavoring agents.

The product form of the deodorizing composition is not particularly limited. For example, it may be in the form of spray, gel, liquid, or solid. A known method can be used for eliminating malodor using the deodorizing composition of the present invention. For example, the deodorizing composition of the present invention in the form of solid, gel, or liquid is directly sprayed, sprinkled, or left on a site or portion where a malodor component (particularly, aldehyde) is present or where a malodor component is predicted to be generated, or such a site or portion is wiped with or immersed in the deodorizing composition. Use of the deodorizing composition by these methods can remove a malodor component or prevent generation of a malodor component. The deodorizing composition of the present invention may be applied by spraying.

The present invention also encompasses a method for screening for a compound having a browning-inhibiting effect on a polyphenol-containing composition. The screening method of the present invention include preparing a sample solution containing a polyphenol, an aldehyde, and a candidate compound; and determining the browning-inhibiting effect of the candidate compound, using as an indicator, the production of a compound represented by the formula (2) in the sample solution.

The compound represented by the formula (2) (Compound (2)) is as described above.

The sample solution may be prepared by any method, but preferably by a method in which a solution containing a polyphenol and a candidate compound is prepared, and the resulting solution is mixed with an aldehyde.

The polyphenol is not limited as long as it is a compound that produces Compound (2) by reactions with aldehydes, and may be suitably selected according to the purpose. For example, in the case of screening for a compound having the browning-inhibiting effect on a green tea beverage, polyphenols such as catechins contained in the green tea beverage may be used. One polyphenol may be used, or two or more polyphenols may be used.

Any aldehyde may be used and suitably selected according to the purpose. For example, in the case of screening for a compound having a browning-inhibiting effect on a green tea beverage, at least one selected from the group consisting of glyoxal, methyl-glyoxal, diacetyl, L-threonine, and 3-deoxy-L-threonine is preferred, and glyoxal is more preferred, for example. These aldehydes are degraded products of L-ascorbic acid that is usually added to green tea beverages, are thus suitable for screening for a candidate compound effective for inhibiting browning in the green tea beverage.

In the present invention, after a sample solution is prepared, it is preferred to monitor the production of Compound (2) in the solution over time. The monitoring time is not particularly limited, and may be suitably set. For example, it is possible to accelerate reaction by subjecting the sample solution to high temperatures in an accelerated test or the like (for example, an autoclave is used at 50° C. to 120° C., preferably 60° C. to 110° C., more preferably 70° C. to 100° C.).

The production of Compound (2) may be detected by any method, such as liquid chromatography-mass spectrometry (LC-MS) of the sample solution, or absorbance measurement. Detection by absorbance measurement is preferred because it is easy to operate.

Compound (2) usually has an absorption maximum at 400 to 600 nm. Thus, the production of Compound (2) can be detected by measuring the absorbance at the above wavelength. For example, the production of Compound (2) can be detected by change in the area under the spectrum at 400 to 600 nm. In addition, as described above, Compound (2) has a pH-dependent absorption maximum. For example, the absorption maximum is around 440 nm near weak acidity (around pH 5), and around 486 to 487 nm at pH 6. 0 to 8. 9 (NE Es-Safi et al. , Food Chem 88 (2004), pp. 367-372). Thus, it is preferred to suitably set the wavelength for detection of Compound (2) according to the pH of the solution. Compound (2) is preferably detected based on its maximum wavelength in the solution. For example, green tea beverages usually have a pH of 6 to 8. In the case of screening for a compound having a browning-inhibiting effect on a green tea beverage, preferably, the absorbance at 487 nm is measured, and the production of Compound (2) is detected by changes in the absorbance at 487 nm.

In the present invention, preferably, the production of Compound (2) is detected by measuring an absorbance spectrum of the sample solution with light having a wavelength of 400 to 600 nm and determining the production based on the amount of change in the area under the absorbance spectrum. It is also preferred to detect the production of Compound (2) by measuring absorbance of the sample solution with light having a wavelength of 487 nm and determining the production based on the amount of change in the absorbance. It is particularly preferred to detect the production of Compound (2) by measuring absorbance of the sample solution with light having a wavelength of 487 nm and determining the production based on changes in the absorbance.

In the screening method of the present invention, preferably, the amount of produced Compound (2) is compared between a sample solution and a control solution containing a polyphenol and an aldehyde but no candidate compound. The amount of produced Compound (2) is compared based on the amount of change in the absorbance between the sample solution and the control solution, with light having a wavelength of 400 to 600 nm, for example. In addition, preferably, the candidate compound is determined as having the browning-inhibiting effect when the presence of the candidate compound resulted in a reduced amount of produced Compound (2) (the production is suppressed) as compared to the case without the candidate compound (control solution) (i.e., when the amount of produced Compound (2) is smaller in the sample solution than in the control solution). For example, the candidate compound used can be determined as having the browning-inhibiting effect when the presence of the candidate compound resulted in a reduced amount of change in the area under the absorbance spectrum at 400 to 600 nm as compared to the case without the candidate compound (i.e., when the amount of change in the area under the absorbance spectrum at 400 to 600 nm is smaller in the sample solution than in the control solution). In addition, for example, in the case of screening for a compound having the browning-inhibiting effect on a green tea beverage, preferably, the candidate compound used is determined as having the browning-inhibiting effect when the presence of the candidate compound resulted in a reduced amount of change in the absorbance at 487 nm as compared to the case without the candidate compound (i.e., when the amount of change in the absorbance at 487 nm is smaller in the sample solution than in the control solution), and such a candidate compound is selected as a browning inhibiting substance.

A substance determined as having the browning-inhibiting effect by the screening method of the present invention can be used for the purposes described above, such as inhibiting browning, scavenging aldehydes, and eliminating odors, and is suitably used as an active ingredient of compositions such as the browning-inhibiting composition, the aldehyde-scavenging composition, and the deodorizing composition.

The present invention also encompasses the following uses and the like of Compound (1).

Use of the compound represented by the formula (1) for inhibiting browning.

Use of the compound represented by the formula (1) for producing a browning-inhibiting composition.

Use of the compound represented by the formula (1) for scavenging aldehydes.

Use of the compound represented by the formula (1) for producing an aldehyde-scavenging composition.

Use of the compound represented by the formula (1) for eliminating odors.

Use of the compound represented by the formula (1) for producing a deodorizing composition.

Use of the compound represented by the formula (1) for suppressing reduction of polyphenols in a polyphenol-containing composition.

Use of the compound represented by the formula (1) for suppressing production of the compound represented by the formula (2) in a polyphenol-containing composition.

An aldehyde-scavenging method including contacting the compound represented by the formula (1) with an aldehyde-containing gas or liquid.

A deodorizing method including contacting the compound represented by the formula (1) with an aldehyde-containing gas or liquid.

Compound (1) and preferred embodiments thereof are as described above. Inhibiting browning is preferably inhibiting browning in a polyphenol-containing composition. Compound (1) is suitably used to eliminate aldehyde-derived odors.

EXAMPLES

The following provides examples that more specifically describe the present invention. The present invention is not limited to these examples.

Measurement of a visible absorption spectrum (400 to 700 nm) was conducted using an ultra-violet and visible spectrophotometer "UV-1700" (Shimadzu Corporation).

In the examples, the visible absorption spectrum is also simply referred to as absorption spectrum.

LC-MS analysis was conducted using a liquid chromatograph-mass spectrometer LC-MS 2020 (Shimadzu Corporation).

Test Example 1

A 2-L PET-bottled green tea beverage was produced and stored unopened at room temperature. Time-dependent changes in color were checked by visual observation and by visible absorption spectrum measurement.

The 2-L PET-bottled green tea beverages were produced by the following method.

Green tea leaves were extracted with 30-fold amount of ion-exchanged water (70° C.) for five minutes. Stirring was performed at minutes 0, 1, 2, 3, and 4 of extraction (five rotations in 15 seconds per time for stirring). At minute 5 of extraction, the tea leave extract was filtered through a 20-mesh filter to remove tea leaves to obtain "extract". This extract was diluted with ion-exchanged water to obtain the amount of the ion-exchanged water used for extraction, and cooled to about 30° C. by running water. The cooled extract was centrifuged at 6000 rpm for 10 minutes, and the supernatant was collected as a diluted solution of the extract. The diluted solution of the extract was passed through a CUNO filter (3M). Ascorbic acid was added to the collected solution, and soda was added as a pH regulator to adjust the pH to 6.4. Further, the resultant solution was diluted with ion-exchanged water to obtain a Brix value of 0.21, thus obtaining a "preparation". The ascorbic acid was added to obtain an ascorbic acid concentration of 0.4 g/L in the preparation. The preparation was sterilized in an ultra-high temperature sterilizer (UHT sterilizer) at 132.5° C. for 60 seconds, and was packed in a 2-L clear PET bottle.

Figure 2:
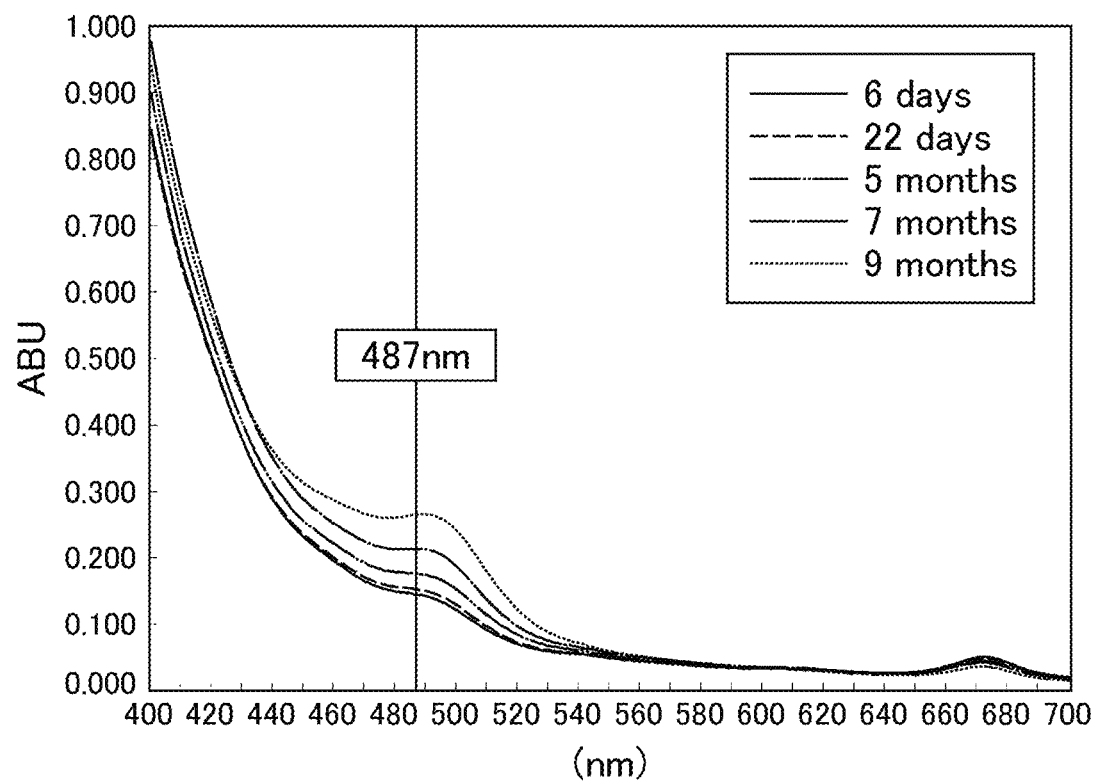
FIG. 2 is a diagram showing visible absorption spectra of the green tea beverages shown in FIG. 1.

The green tea beverage on day 6 after production exhibited light yellow, but turned into yellowish brown as the storage period prolonged. The visible absorption spectrum of each green tea beverage was measured, and it was found that the absorption spectrum with a maximum wavelength at 487 nm increased along with changes in tinge of color observed visually. FIG. 1 is a picture showing the appearance of PET-bottled green tea beverages individually stored for 6 days, 22 days, 5 months, 7 months, and 9 months at room temperature. FIG. 2 is a diagram showing visible absorption spectra of the green tea beverages shown in FIG. 1. Based on these results, the absorption intensity at 487 nm was used as an indicator of browning in a green tea beverage.

Test Example 2

Green tea leaves were extracted with 30-fold amount of ion-exchanged water (70° C.) for five minutes. Stirring was performed at minutes 0, 1, 2, 3, and 4 of extraction (five rotations in 15 seconds per time for stirring). At minute 5 of extraction, the tea leave extract was filtered through a 20-mesh filter to remove tea leaves to obtain "extract". This extract was diluted with ion-exchanged water to obtain the amount of the ion-exchanged water used for extraction, and cooled to about 30° C. by running water. The cooled extract was centrifuged at 6000 rpm for 10 minutes, and the supernatant was collected as a diluted solution of the extract. The diluted solution of the extract was passed through a CUNO filter (3M). Ascorbic acid was added to the collected solution, and soda was added as a pH regulator to adjust the pH to 6.4. Further, the resultant solution was diluted with ion-exchanged water to obtain a Brix value of 0.21, thus obtaining a "preparation". The ascorbic acid was added to obtain an ascorbic acid concentration of 0, 0.04, 0.4, or 1.2 g/L in the preparation.

The preparation prepared above was subjected to an aging test under the following conditions, and then the visible absorption spectrum was measured. Condition 1: purged with nitrogen, stored at 4° C. for one hour Condition 2: stored at 121° C. for 14 minutes Condition 3: after oxygen aeration, stored at 123° C. for 30 minutes Conditions 2 and 3 are accelerated aging tests in an autoclave. Condition 2 is based on assumptions that sterilization is performed during production of a green tea beverage. In condition 2, neither oxygen aeration nor nitrogen purging were performed. Condition 3 is based on assumptions that the browning reaction has reached maximum due to excess oxygen.

Figure 3:
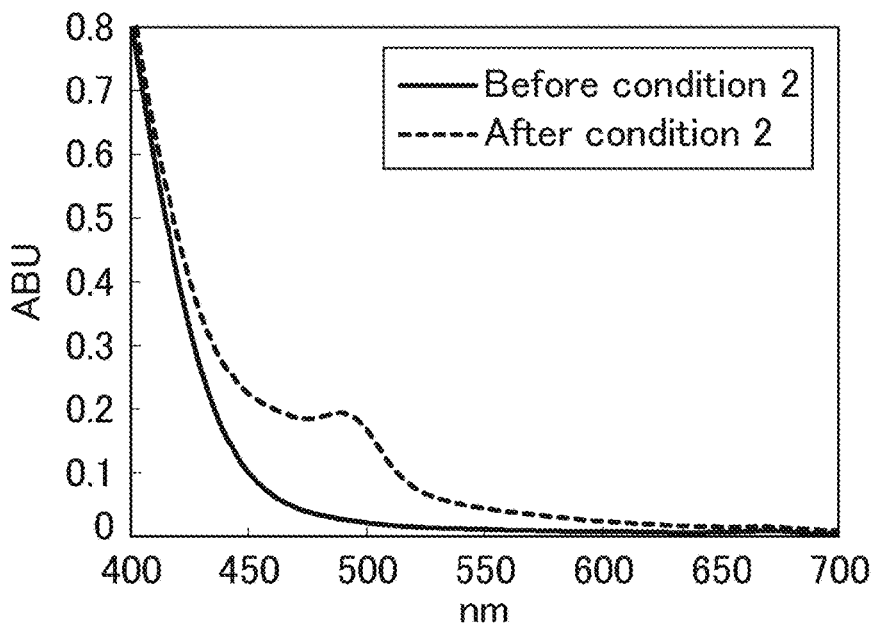
FIG. 3 is a diagram showing visible absorption spectra of a preparation to which 0.4 g/L of ascorbic acid was added, before and after an aging test under condition 2.

FIG. 3 and FIG. 4 show the results.

FIG. 3 is a diagram showing visible absorption spectra of a preparation to which 0.4 g/L of ascorbic acid was added, before and after an aging test under condition 2. In FIG. 3, the solid line indicates a spectrum before a test under condition 2, and the dashed line indicates a spectrum after the test.

Figure 4A:
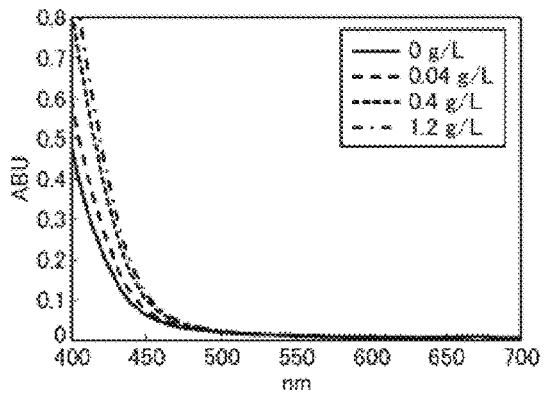
FIGS. 4(a) to 4(c) are diagrams showing visible absorption spectra of preparations after aging tests (FIG. 4(a): condition 1 (purged with nitrogen, stored at 4° C. for one hour), FIG. 4(b): condition 2 (stored at 121° C. for 14 minutes), FIG. 4(c): condition 3 (after oxygen aeration, stored at 123° C. for 30 minutes)).
Figure 4B:
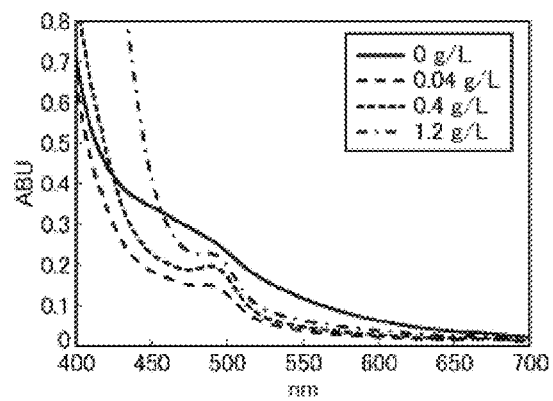
Figure 4C:
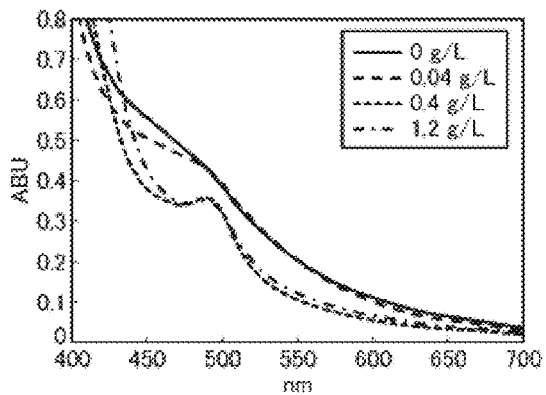

FIGS. 4(a) to 4(c) are diagrams showing visible absorption spectra of preparations after aging tests (FIG. 4(a): condition 1 (purged with nitrogen, stored at 4° C. for one hour), FIG. 4(b): condition 2 (stored at 121° C. for 14 minutes), FIG. 4(c): condition 3 (after oxygen aeration, stored at 123° C. for 30 minutes)).

In FIG. 4(a) to FIG. 4(c), the solid line indicates a preparation to which 0 g/L of ascorbic acid was added; the dashed line indicates a preparation to which 0.04 g/L of ascorbic acid was added; the dotted line indicates a preparation to which 0.4 g/L of ascorbic acid was added; and the long dashed dotted line indicates a visible absorption spectrum of a preparation to which 1.2 g/L of ascorbic acid was added.

FIG. 3 reveals that the preparation under condition 2 (stored at 121° C., 14 min) increased its absorption at 450 to 550 nm. In particular, the preparation exhibited a marked increase in the absorption maximum at 487 nm.

As shown in FIG. 4(a), there are differences in the absorption at 400 to 450 nm under condition 1 (purged with nitrogen, stored at 4° C.), but none of the spectra showed an absorption maximum.

The results under condition 2 (stored at 121° C., 14 min) (FIG. 4(b)) show that the preparations containing ascorbic acid each exhibited lower absorption around 500 to 600 nm than the preparation to which no ascorbic acid was added. An absorption wavelength band around 500 to 600 nm looked red by visual observation, so that addition of ascorbic acid was considered to suppress production of a compound that exhibits red (such as proanthocyanidin that is produced by oxidative polymerization of catechin itself).

According to visual observation of the samples, only the ascorbic acid-free preparation markedly exhibits red. Thus, compounds derived from the green tea were considered to react with each other, producing a red compound.

According to the results under condition 2 shown in FIG. 4(b), the absorption increased around 450 to 500 nm (absorption maximum value: 487 nm) according to the amount of ascorbic acid. The absorption wavelength band around 450 to 500 nm looked yellow to brown by visual observation. Thus, addition of ascorbic acid was considered to produce a compound that exhibit yellow to brown.

Also according to visual observation of a sample, addition of ascorbic acid resulted in yellowish brown, and a yellowish brown compound was considered to be produced with ascorbic acid as a substrate.

According to the results of condition 3 (after oxygen aeration, stored at 123° C. for 30 minutes) (FIG. 4(c)), the preparation to which a small amount of ascorbic acid was added exhibited a similar spectrum as that of the ascorbic acid-free preparation when the browning reaction reached the maximum. Loss of oxidation inhibiting effect due to loss of ascorbic acid is considered to result in the same reaction product as that produced in the case of the ascorbic acid-free preparation.

If subjected to further oxygen aeration and heating, the preparation having an ascorbic acid concentration of 0.4 g/L or more is also considered to be ultimately in a state close to the above state.

These results show that the accelerated aging time can be shortened by high temperature conditions, and browning phenomena can be traced. At the same time, it was found that ascorbic acid significantly contributed to color tone deterioration and that ascorbic acid was a substrate that contributes to an increase in the absorption maximum at 487 nm (yellowish browning) used as an evaluation indicator of browning.

Test Example 3

Ascorbic acid was found to be a substrate in the reaction that causes browning in green tea beverages. Thus, another experiment was performed to search the other compound reactive with the ascorbic acid and responsible for yellowish browning using a technique in natural products chemistry. As a result, catechins, which are a type of polyphenols, were selected. Four kinds of catechins, i.e., epicatechin (EC), epigallocatechin (EGC), epicatechin gallate (ECg), and epigallocatechin gallate (EGCg), were listed as candidates. These catechins undergo epimerization when heat-sterilized, producing isomers such as catechin (C), gallocatechin (GC), catechin gallate (Cg), and gallocatechin gallate (GCg).

The following model experiment was performed to investigate browning in the green tea at the compound level.

Figure 5:
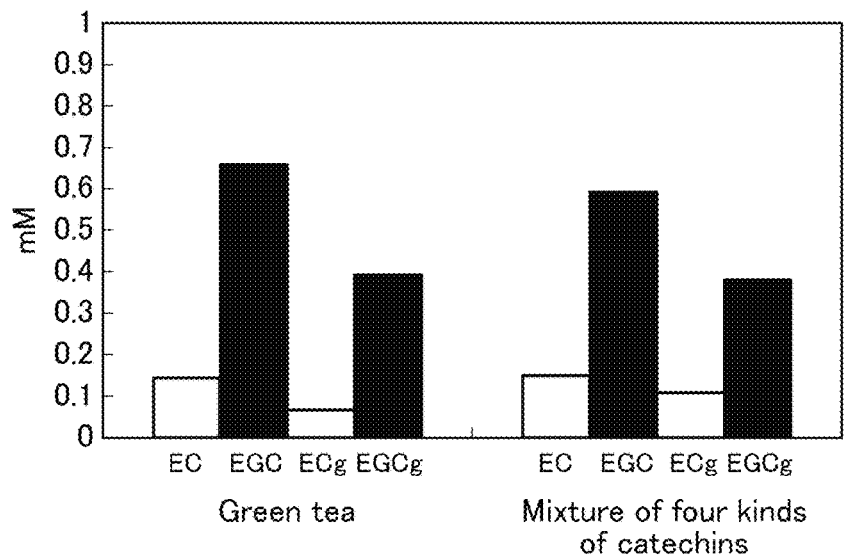
FIG. 5 is a diagram showing concentrations of epicatechin (EC), epigallocatechin (EGC), epicatechin gallate (ECg), and epigallocatechin gallate (EGCg) in green tea and a model solution (containing four kinds of catechins).

The diluted solution of the extract in Test Example 2 was used as green tea. A model solution was prepared as a mixture of four kinds of catechins in which the concentrations of the four kinds of catechins were adjusted to be equivalent to those in the green tea. FIG. 5 is a diagram showing concentrations of epicatechin (EC), epigallocatechin (EGC), epicatechin gallate (ECg), and epigallocatechin gallate (EGCg) in the green tea and a model solution (containing four kinds of catechins). Theses concentrations were measured by LC-MS.

LC-MS measurement conditions for catechins
LC
Column: 2.5 Cholester (Nacalai Tesque, Inc.) (100 mmL.× 2.0 I.D.)
Mobile phase:
A: 0.1% formic acid/$H_2O$
B: 0.1% formic acid/$CH_3CN$
Gradient elution method
Time program (concentration of B solution is expressed in percent by volume): B 5% (0-0.5 min)→B 32% (20 min)→B 100% (25-27.5 min)→B 5% (27.51-30 min)
Flow rate: 0.25 mL/min
Column temperature: 40° C.
Sample injection volume: 2 μL
MS
Probe voltage:
+4.5 kV (ESI positive mode)
−3.5 kV (ESI negative mode)
Nebulizer gas flow rate: 1.5 L/min
Drying gas flow rate: 20 L/min
DL temperature: 250° C.
DL voltage/Q-array voltage: default value SIM:

m/z 289 (negative) (EC)
m/z 305 (negative) (EGC)
m/z 441 (negative) (ECg)
m/z 457 (negative) (EGCg)

Dehydroascorbic acid (0.4 g/L) as a reaction substrate and soda as a pH regulator in an adequate amount were added to the green tea and the model solution, and the pH was adjusted to 6.4. These mixtures were subjected to accelerated aging test. It has been found by various experiments that browning is promoted by dehydroascorbic acid which is an oxidized ascorbic acid. An experimental system was created which simulates a state in which the ascorbic acid as an antioxidant was entirely oxidized.

The green tea and the model solution (containing four kinds of catechins) were accelerated-aged in an autoclave under condition 3 (after oxygen aeration, stored at 123° C. for 30 minutes) in Test Example 2, and behaviors of the visible absorption spectrum were observed.

Figure 6A:
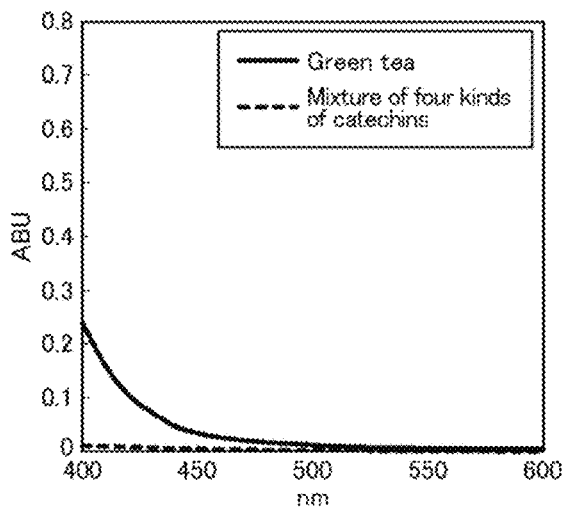
FIG. 6(a) is a diagram showing visible absorption spectra of the green tea and the model solution (containing four kinds of catechins) before an accelerated aging test.
Figure 6B:
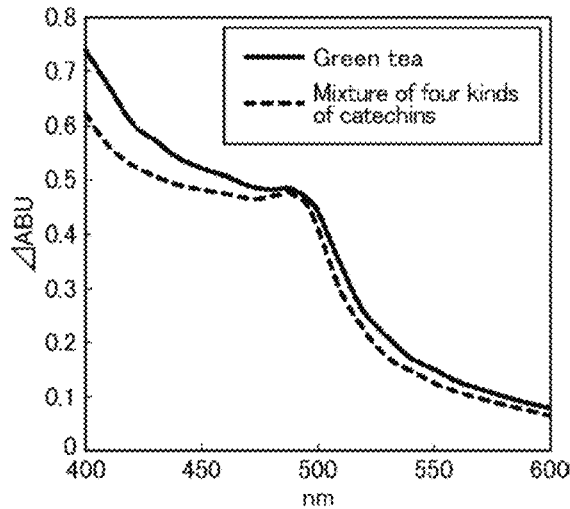
FIG. 6(b) is a diagram showing the amount of change in absorption (AABU) of the green tea and the model solution before and after accelerated aging.

FIG. 6(a) is a diagram showing visible absorption spectra of the green tea and the model solution (containing four kinds of catechins) before an accelerated aging test; and FIG. 6(b) is a diagram showing the amount of change in absorption (AABU) of the green tea and the model solution before and after accelerated aging. In each of FIGS. 6(a) and 6(b), the solid line indicates the green tea, and the dashed line indicates the model solution (containing four kinds of catechins).

As shown in FIGS. 6(a) and 6(b), the amount of change (AABU) before and after accelerated aging was substantially the same between the spectrum of the green tea and the spectrum of the model solution containing four kinds of catechins. In addition, these spectra are also highly similar to each other in terms of an increase in the absorption maximum at 487. Thus, it is considered that a reaction similar to the browning reaction in the green tea was reproduced by the model solution. From these results, catechins and ascorbic acid (and soda) were found as a group of components responsible for browning in the green tea.

Test Example 4

There are two kinds of degradation pathways of ascorbic acid: a pathway in which an aldehyde is produced through oxidization of ascorbic acid into dehydroascorbic acid; and a pathway in which an aldehyde is produced without oxidization of ascorbic acid into dehydroascorbic acid. It has been reported that aldehydes such as glyoxal, methyl-glyoxal, diacetyl, L-threonine, and 3-deoxy-L-threonine are produced as degraded products in each pathway (A Schulz et al., Int J Mass Spec 262 (2007), pp. 169-173).

An examination was performed to investigate what kinds of aldehydes were actually produced in the presence of ascorbic acid and soda.

A solution containing a mixture of ascorbic acid (0.4 g/L) and soda (0.37 g/L) which are used in green tea beverages was prepared. The solution was subjected to an accelerated aging test under condition 3 (after oxygen aeration, stored at 123° C. for 30 minutes) in Test Example 2, and the resulted aldehydes were analyzed by LC-MS. The aldehydes were derivatized with o-(4-cyano-2-ethoxybenzyl)hydroxylamine (CNET) sulfate, and detected by LC-MS. Derivatization with CNET sulfate was performed by adding a 1% aqueous solution of CNET sulfate (Hayashi Pure Chemical Ind., Ltd., product name "CNET glyoxal solution") (0.5 mL) to a sample (5 mL) for a reaction at room temperature for two hours. The solution after the reaction was filtered through a filter (0.2μ), and subjected to LC-MS under the following conditions. FIG. 7 shows LC-MS measurement results.
LC-MS measurement conditions
LC
Column: C18M 2D (Shodex) (100 mmL.×2.0 I.D.)
Mobile phase:
A: 0.1% formic acid/$H_2O$
B: 0.1% formic acid/$CH_3CN$
Gradient elution method
Time program (concentration of B solution is expressed in percent by volume): B 5% (0-2 min)→B 60% (7.5 min)→B 100% (17-21 min)→B 5% (22-30 min)
Flow rate: 0.2 mL/min
Column temperature: 40° C.
Sample injection volume: 2 μL
MS
Probe voltage:
  +1.6 kV (ESI positive mode)
  −1.6 kV (ESI negative mode)
Nebulizer gas flow rate: 1.5 L/min
Drying gas flow rate: 20 L/min
DL temperature: 250° C.
DL voltage/Q-array voltage: default value
SIM:

m/z 195 (negative)
m/z 249 (negative)
m/z 407 (positive)

Figure 7A:
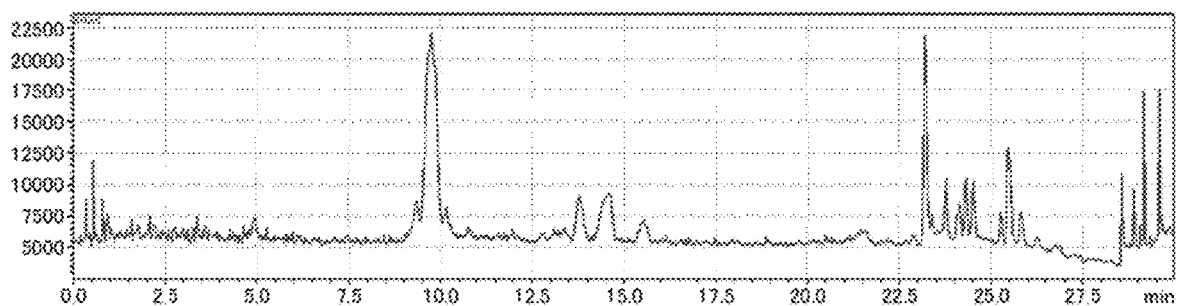
FIGS. 7(a) and 7(b) are respectively a chromatogram (SCAN data) obtained by scan mode liquid chromatography-mass spectrometry (LC-MS) analysis of CNET-derivatized degraded products of ascorbic acid; and a chromatogram (SIM data) obtained by selective ion monitoring (SIM) mode liquid chromatography-mass spectrometry (LC-MS) analysis of the same (FIG. 7(a): SCAN data, FIG. 7(b): SIM data).
Figure 7B:
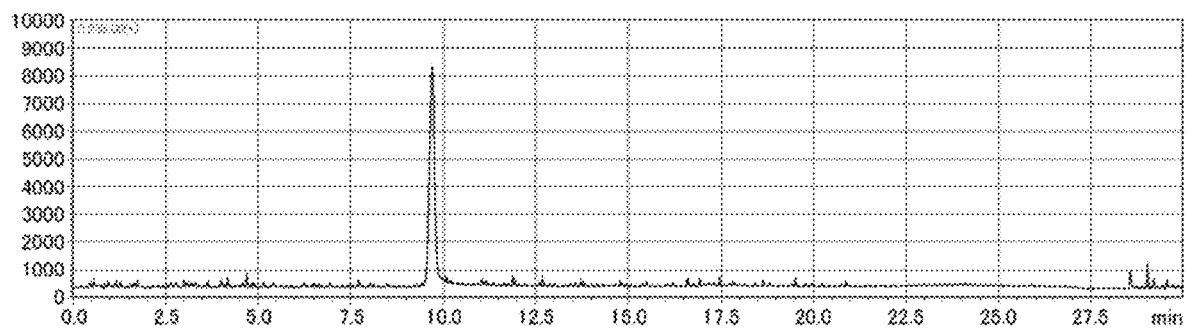

FIGS. 7(a) and 7(b) are respectively a chromatogram (SCAN data) obtained by scan mode LC-MS analysis of CNET-derivatized degraded products of ascorbic acid; and a chromatogram (SIM data) obtained by selective ion monitoring (SIM) mode LC-MS analysis of the same (FIG. 7(a): SCAN data, FIG. 7(b): SIM data). The detected peak was qualitatively confirmed to be CNET derivatized glyoxal. The result reveals that glyoxal which is an aldehyde was produced from ascorbic acid in the green tea.

Test Example 5

According to the results of Test Examples 1 to 4, it was considered that the compound produced by the reaction of glyoxal derived from ascorbic acid with a catechin as a reaction substrate was highly likely a substance that causes browning in green tea beverages. An experiment was performed to investigate the possibility.

A mixture (green tea model) of epicatechin (EC) (0.5 g/L) and glyoxal (0.01 g/L) was accelerated-aged under condition 3 (after oxygen aeration, stored at 123° C. for 30 minutes) in Test Example 2, and analyzed by LC-MS under the following conditions.
LC-MS measurement conditions
LC
Column: 2.5 Cholester (Nacalai Tesque, Inc.) (100 mmL.× 2.0 I.D.)
Mobile phase:
A: 0.1% formic acid/$H_2O$
B: 0.1% formic acid/$CH_3CN$
Gradient elution method
Time program (concentration of B solution is expressed in percent by volume): B 5% (0-0.5 min)→B 32% (20 min)→B 100% (25-27.5 min)→B 5% (27.51-30 min)
Flow rate: 0.25 mL/min
Column temperature: 40° C.
Sample injection volume: 2 μL
MS
Probe voltage:
  +4.5 kV (ESI positive mode)
  −3.5 kV (ESI negative mode)
Nebulizer gas flow rate: 1.5 L/min
Drying gas flow rate: 20 L/min
DL temperature: 250° C.
DL voltage/Q-array voltage: default value
SCAN: m/z 100-800 (positive, negative)

SIM:

| |
|---|
| m/z 289 (negative) (EC) |
| m/z 347 (negative) |
| m/z 601 (negative) |

Figure 8:
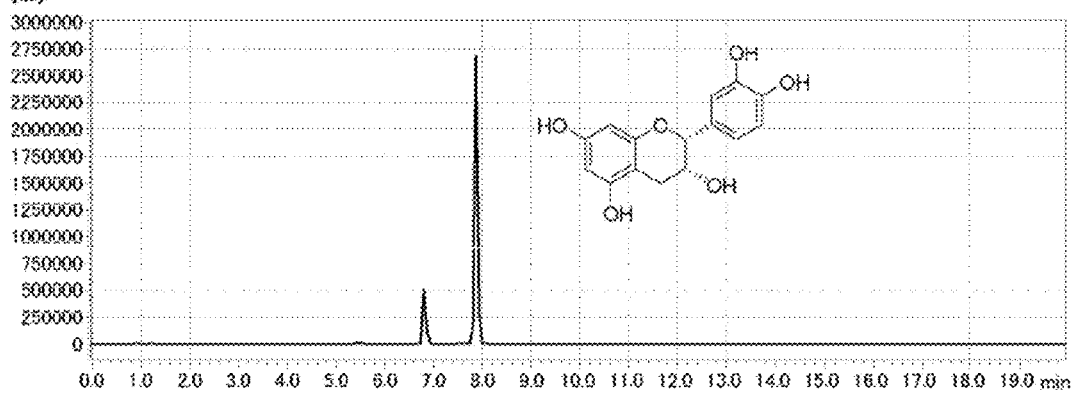
FIGS. 8(a) to 8(d) are chromatograms obtained by SIM mode LC-MS analysis of epicatechin, a compound in which one epicatechin molecule and one glyoxal molecule are bonded together, and a compound having a xanthylium structure in which two epicatechin molecules and one glyoxal molecule are bonded together, which were detected in an accelerated-aged green tea model (FIG. 8(a): a chromatogram of epicatechin, FIG. 8(b): a chromatogram of the compound in which one epicatechin molecule and one glyoxal molecule are bonded together, FIG. 8(c): a chromatogram of the compound having a xanthylium structure in which two epicatechin molecules and one glyoxal molecule are bonded together, FIG. 8(d): the chromatograms (a) to (c) that are overlaid together).
Figure 8:
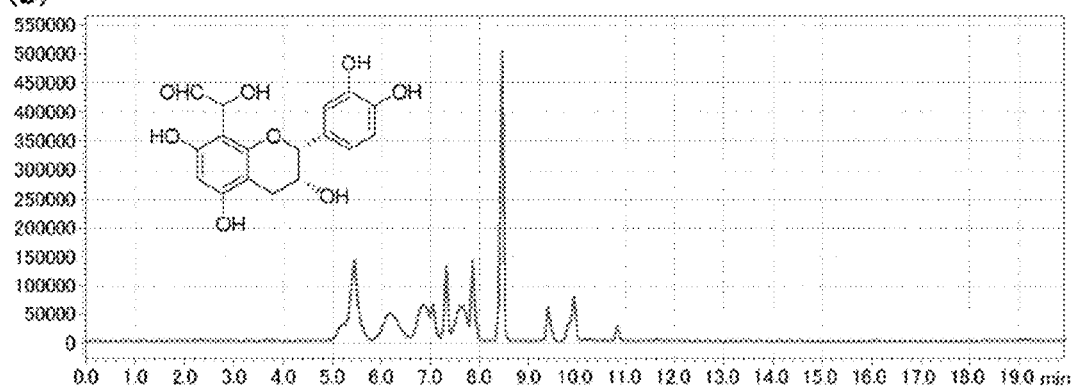
Figure 8:
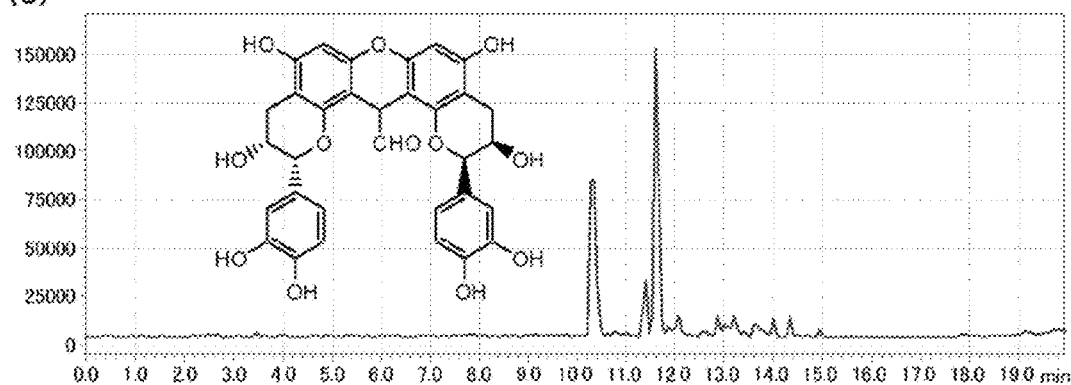
Figure 8:
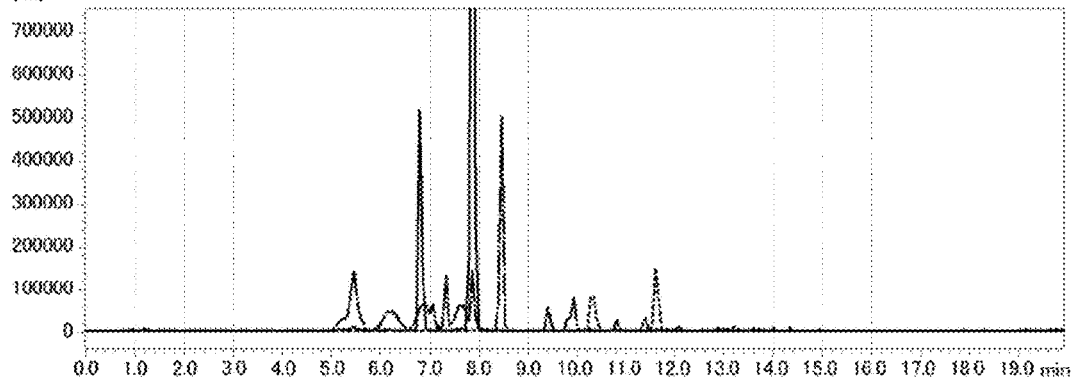

FIGS. 8(a) to 8(d) are chromatograms obtained by SIM mode LC-MS analysis of epicatechin, a compound in which one epicatechin molecule and one glyoxal molecule are bonded together, and a compound having a xanthylium structure in which two epicatechin molecules and one glyoxal molecule are bonded together, which were detected in the accelerated-aged green tea model (FIG. 8(a): a chromatogram of epicatechin, FIG. 8(b): a chromatogram of the compound in which one epicatechin molecule and one glyoxal molecule are bonded together, FIG. 8(c): a chromatogram of the compound having a xanthylium structure in which two epicatechin molecules and one glyoxal molecule are bonded together, FIG. 8(d): the chromatograms (a) to (c) that are overlaid together). As shown in FIGS. 8(a) to 8(d), in addition to an unreacted epicatechin (monomer) (chemical formula: $C_{15}H_{14}O_6$, molecular weight: 290.08, FIG. 8(a)), the following compounds produced by accelerated aging were detected: a compound in which one epicatechin molecule and one glyoxal molecule are bonded together (chemical formula: $C_{17}H_{16}O_8$, molecular weight: 348.08, FIG. 8(b)) (colorless); and a compound having a xanthylium structure in which two epicatechin molecules and one glyoxal molecule are bonded together (brown) (chemical formula: $C_{32}H_{26}O_{12}$, molecular weight: 602.14, FIG. 8(c)).

This result reveals that the browning reaction in the green tea was successfully traced using the compounds as models.

The compound having a xanthylium structure has an absorption maximum around 487 nm near neutral which is a pH of green tea beverages (NE Es-Safi et al., Food Chem 88 (2004), pp. 367-372). Thus, the production of a compound having a xanthylium structure (browning) in a solution such as a green tea beverage whose pH is near neutral can be evaluated by changes in absorption at 487 nm.

Example 1

It was found that browning in the green tea was caused by reactions of catechins with aldehydes. It became clear from another experiment that the reactions with aldehydes also occur with compounds having a flavonoid skeleton, other than catechins.

Using such properties of compounds having a flavonoid skeleton, a search was performed for a flavonoid compound which reacts with an aldehyde even under competition with catechins in the green tea and whose reaction product does not exhibit a color.

The compound having a xanthylium structure (brown) detected in Test Example 5 was formed as follows: one aldehyde molecule reacted with two catechin molecules to produce a carboxymethine-crosslinked dimer of the catechin; and in the dimer, catechin-derived hydroxyl groups (hydroxyl groups each bonded to a carbon atom adjacent to a carbon atom that reacted with the aldehyde) underwent dehydration reaction to effect ring closure. Thus, in the case of a compound having a flavone skeleton as an example of compounds having a browning-inhibiting effect, an effective compound was considered to be one whose hydroxyl group bonded to a carbon atom at a position ortho to a carbon atom of the A-ring which reacts with an aldehyde is protected.

Specifically, a compound having a structure of the following formula (I) was considered as an example of candidate compounds.

[Chem. 8]

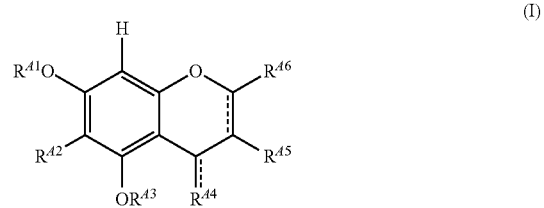

(I)

In the formula, a dashed line may represent a double bond. In the compound represented by the formula, at least position 8 of the A-ring (benzene ring) is a position at which a reaction occurs with an aldehyde. $R^{A1}$ is a substituent. The hydroxyl group at position 7 adjacent to position 8 at which the reaction occurs with an aldehyde is protected ($OR^{A1}$). $R^{A2}$ is a hydrogen atom or a substituent. When $R^{A2}$ is a hydrogen atom, the carbon atom to which $R^{A2}$ is bonded can react with an aldehyde, and in such a case, $R^{A3}$ is a substituent. $R^{A4}$ is a hydrogen atom, an oxygen atom, or a substituent. $R^{A5}$ and $R^{A6}$ are each independently a hydrogen atom, a substituent, or the like.

As a flavonoid having the above structure, baicalin (FUJI-FILM Wako Pure Chemical Corporation) was used for experiments. The structural formula of baicalin is shown below.

[Chem. 9]

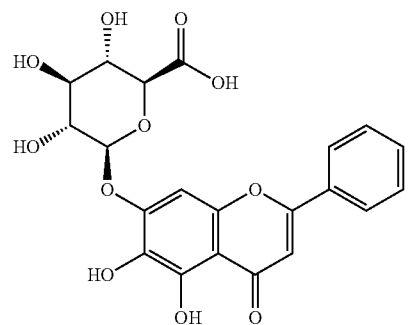

Baicalin (0.5 g/L) was added to a model solution obtained by mixing epicatechin (0.5 g/L) with glyoxal (0.01 g/L). The mixture was accelerated-aged under condition 3 (after oxygen aeration, stored at 123° C. for 30 minutes) in Test Example 2, and the amount of change in the visible absorption spectrum (ΔABU) before and after accelerated aging was calculated.

Figure 9:
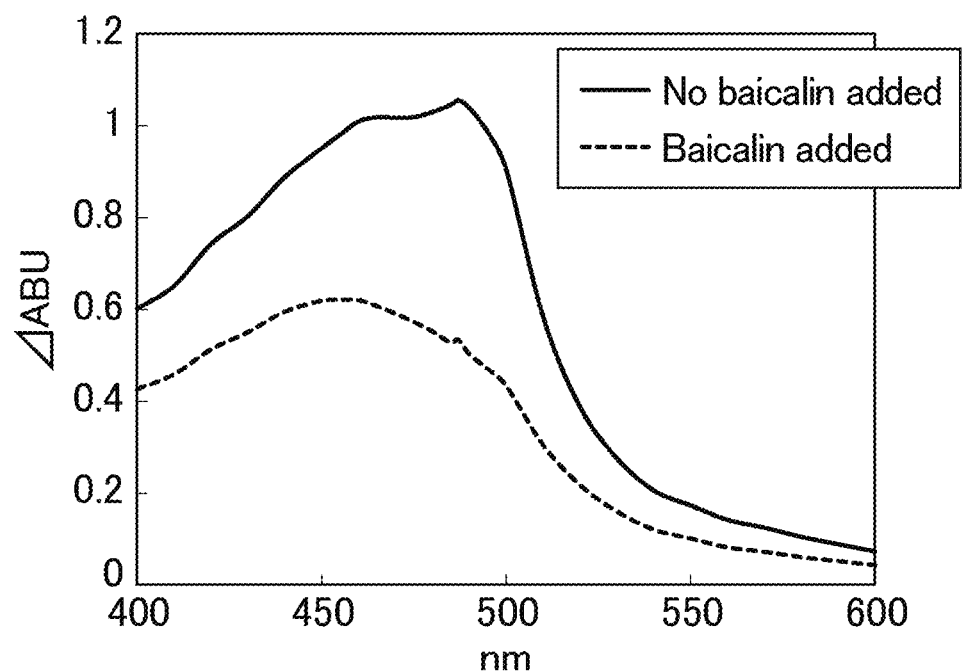
FIG. 9 is a diagram showing changes in a visible absorption spectrum of a model solution by addition of baicalin.

FIG. 9 is a diagram showing changes in a visible absorption spectrum of the model solution by addition of baicalin.

As shown in FIG. 9, the amount of change in the visible absorption spectrum (ΔABU) before and after accelerated aging was significantly reduced by adding baicalin (dashed line), compared to the case where no baicalin was added (solid line).

Example 2

The following three kinds of solutions were prepared.
B+G: a mixture of baicalin (0.5 g/L) and glyoxal (0.01 g/L)

B+C+G: a mixture of baicalin (0.5 g/L), epicatechin (0.5 g/L), and glyoxal (0.01 g/L) C+G: a mixture of epicatechin (0.5 g/L) and glyoxal (0.01 g/L)

These solutions were kept in an autoclave at 121° C. for 15 minutes for accelerated aging. After accelerated aging, changes in color were checked by visual observation, and further, the visible absorption spectrum was measured. FIG. 10 shows the results.

Figure 10A:
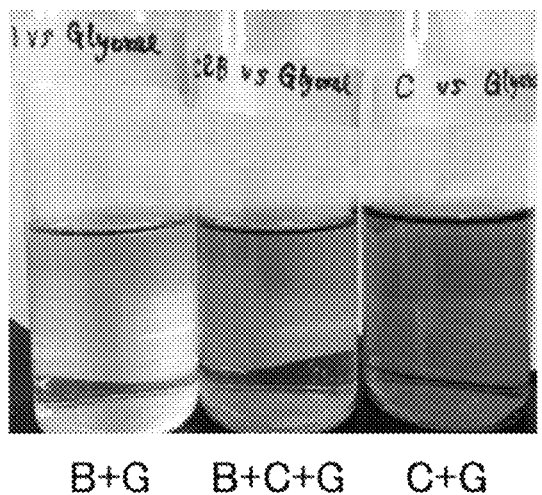
FIG. 10(a) is a picture showing the appearance of a mixture of baicalin and glyoxal (B+G), a mixture of baicalin, epicatechin, and glyoxal (B+C+G), and a mixture of epicatechin and glyoxal (C+G) after accelerated aging.
Figure 10B:
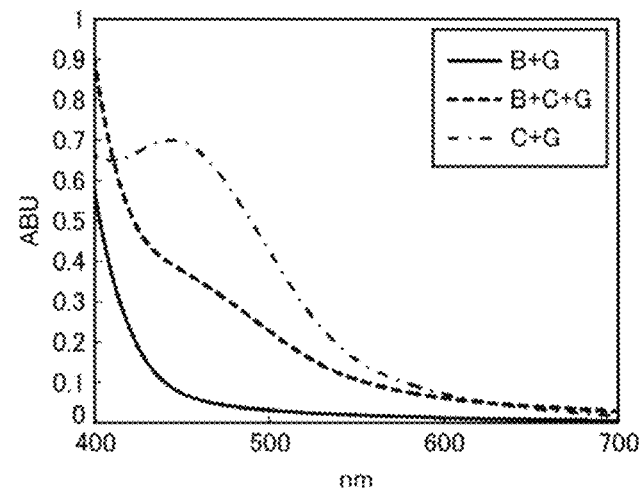
FIG. 10(b) is a diagram showing visible absorption spectra of the same (FIG. 10(a): picture, (b): visible absorption spectra).

FIG. 10(a) is a picture showing the appearance of the mixture of baicalin and glyoxal (B+G), the mixture of baicalin, epicatechin, and glyoxal (B+C+G), and the mixture of epicatechin and glyoxal (C+G) after accelerated aging; and FIG. 10(b) is a diagram showing visible absorption spectra of the same (FIG. 10(a): picture, (b): visible absorption spectra). In FIG. 10(b), the solid line indicates the mixture (B+G), the dashed line indicates the mixture (B+C+G), and the long dashed dotted line indicates the mixture (C+G).

According to visual observation of the colors of the mixtures (B+G), (B+C+G), and (C+G), the mixture (B+G) exhibited light yellow and the mixture (C+G) exhibited brown. At this point, the mixture (B+C+G) exhibited yellowish brown which is between the colors of the mixtures (B+G) and (C+G). Comparison between the mixture (B+C+G) and the mixture (C+G) shown in FIG. 10(b) reveals that addition of baicalin significantly reduces the absorption at 487 nm. This indicates that baicalin inhibitedbrowningwhich results from epicatechin and aldehyde.

The results of Example 1 and Example 2 demonstrated the browning-inhibiting effect of baicalin.

Further, after accelerated aging, the amount of epicatechin (the amount of a residual catechin) in the mixture (B+C+G) and the mixture (C+G) was measured by LC-MS under the same conditions as in Test Example 3.

Figure 11:
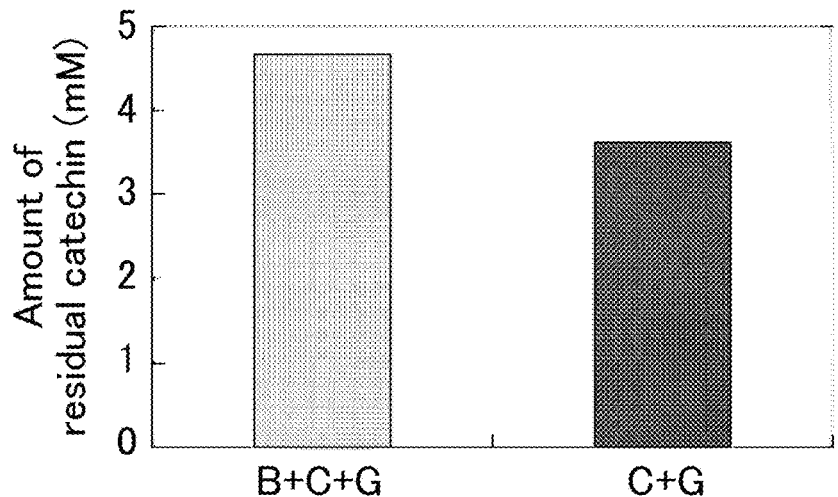
FIG. 11 is a graph showing the amount (mM) of a residual catechin in the mixture (B+C+G) and the mixture (C+G) after accelerated aging.

FIG. 11 shows the amount (mM) of the residual catechin in the mixture (B+C+G) and the mixture (C+G) after accelerated aging. FIG. 11 reveals that addition of baicalin increases the amount of the residual catechin in a solution.

Example 3

The mechanism of the browning-inhibiting effect of baicalin was investigated.

A mixture of baicalin (0.5 g/L) and glyoxal (0.01 g/L) was accelerated-aged under condition 3 (after oxygen aeration, stored at 30 min at 123° C.) of Test Example 2, and analyzed by LC-MS. LC-MS measurement conditions are the same as those in Test Example 5.

Figure 12A:
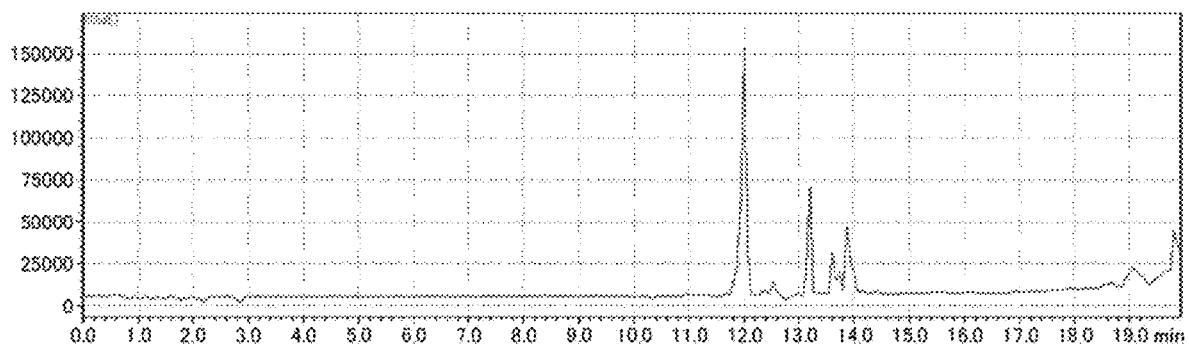
FIGS. 12(a) and 12(b) are chromatograms obtained by SIM mode LC-MS analysis of compounds detected in a solution obtained by accelerated aging of a mixture of baicalin and glyoxal (FIG. 12(a): a compound in which one glyoxal molecule and one baicalin molecule are bonded together, FIG. 12(b): baicalin).
Figure 12B:
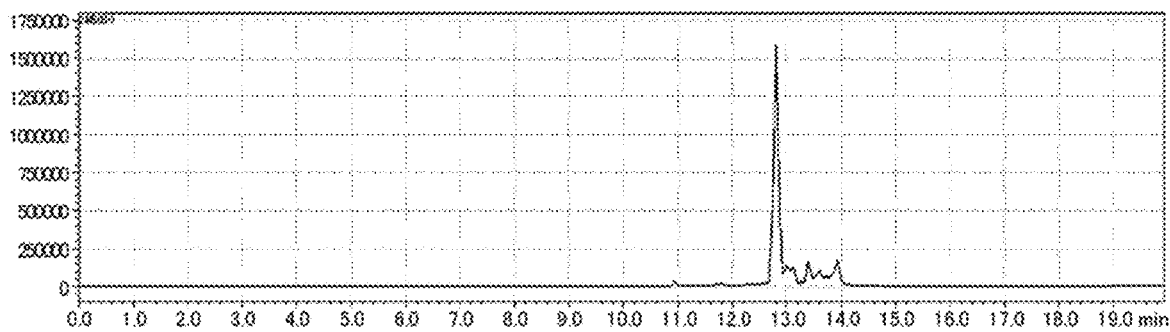

FIGS. 12(a) and 12(b) are chromatograms obtained by SIM mode LC-MS analysis of compounds detected in the solution obtained by accelerated aging of the mixture of baicalin and glyoxal (FIG. 12(a): a compound in which one glyoxal molecule and one baicalin molecule are bonded together, FIG. 12(b): baicalin). A peak indicated by an arrow in FIG. 12(a) corresponded to baicalin (unreacted baicalin). A peak indicated by an arrow in FIG. 12(b) corresponded to a compound having the following structural formula (II) in which one baicalin molecule and one glyoxal molecule were bonded together. A reaction scheme of glyoxal with baicalin and a reaction product are shown below.

[Chem. 10]

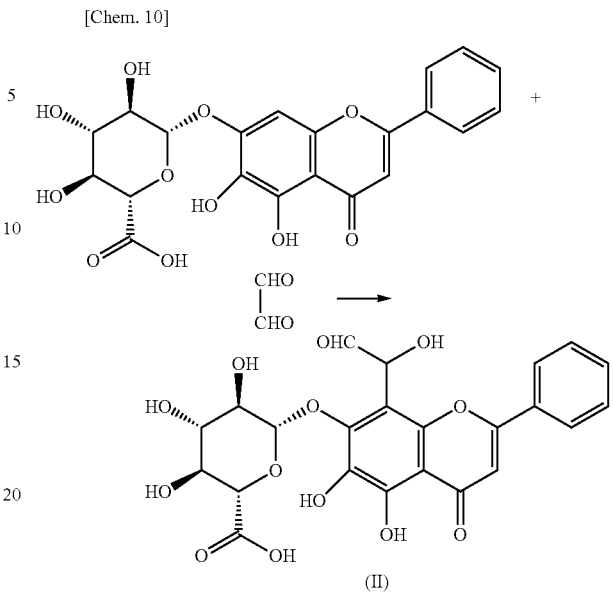

No compound having a xanthylium structure that exhibits brown was detected. Thus, it was assumed that baicalin reacted with glyoxal (aldehyde) under competition with catechins in the green tea, and no compound having a xanthylium structure was thus produced.

<Preparation 1>

Baicalin glycoside was prepared by the following method in order to increase the solubility of baicalin in water.

Sodium ascorbate (2.5 g) was dissolved in distilled water (500 mL). 1 N NaOH (20 mL) was added to the solution and the pH was adjusted to 12, thus preparing an aqueous solution of sodium ascorbate. Baicalin (FUJIFILM Wako Pure Chemical Corporation) (500 mg) and dextrin (derived from maize) (2500 mg) were added to the aqueous solution of sodium ascorbate (500 mL). 1 N HCl (4 mL) was added to the mixture, and the pH was adjusted to 7.0. Then, glycosyltransferase (Contizyme, Amano Enzyme Inc.) (100 U) was added to the mixture. After a reaction at 68° C. for 35 hours, the mixture was heated at 95° C. for 30 minutes to deactivate the enzyme.

The reaction mixture was passed through a column packed with Diaion HP20 (Mitsubishi Chemical Corporation) (1000 mL) (food additive ethanol (2 L) and subsequently distilled water (2 L) had been passed through the column in advance), and distilled water (2 L) was then passed therethrough. Subsequently, the column was eluted with 80% ethanol (2 L). Then, 80% ethanol fraction was concentrated in an evaporator, and freeze-dried. The 80% ethanol fraction (fractions Nos. 1 to 8) was analyzed by LC-MS under the following conditions to quantify the baicalin content. Table 1 shows the baicalin glycoside (glycosylated baicalin) yield in the 80% ethanol fraction (the fractions Nos. 1 to 8).

LC-MS analysis conditions for baicalin
 LC
Column: C18M 2D (Shodex) (100 mmL.×2.0 I.D.)
Mobile phase:
A: 0.1% formic acid/$H_2O$
B: 0.1% formic acid/$CH_3CN$
Gradient elution method
Time program (concentration of B solution is expressed in percent by volume): B 5% (0-2 min)→B 28% (10 min)→B 50% (15 min)→B 100% (18 min)→B 5% (20-26 min)

Flow rate: 0.2 mL/min
Column temperature: 25° C.
Sample injection volume: 2 μL
MS
Interface DUIS (ESI & APCI)
Nebulizer gas flow rate: 1.5 L/min
Drying gas flow rate: 20 L/min
DL temperature: 250° C.
DL voltage/Q-array voltage: default value
SIM: m/z 447 (positive) (baicalin)

The presence or absence of glycosylation was determined by LC-MS under the following measurement conditions.
LC-MS analysis conditions for baicalin glycosides
LC
Column: C18M 2D (Shodex) (100 mmL.×2.0 I.D.)
Mobile phase:
A: 0.1% formic acid/H$_2$O
B: 0.1% formic acid/CH$_3$CN
Gradient elution method
Time program (concentration of B solution is expressed in percent by volume): B 12.5% (0-0.5 min)→B 25% (10 min)→B 50% (20-22 min)→B 12.5% (24-26 min)
Flow rate: 0.2 mL/min
Column temperature: 25° C.
Sample injection volume: 2 μL
MS
Interface DUIS (ESI & APCI)
Nebulizer gas flow rate: 1.5 L/min
Drying gas flow rate: 20 L/min
DL temperature: 250° C.
DL voltage/Q-array voltage: default value
SIM:

| |
|---|
| m/z 447 (positive) baicalin |
| m/z 609 (positive) baicalin monoglucoside |
| m/z 771 (positive) baicalin diglucoside |
| m/z 933 (positive) baicalin triglucoside |

TABLE 1

| Fraction No. | Mass (g) | Baicalin (g) | Baicalin glycoside (g) |
|---|---|---|---|
| 1 | 0 | 0.0015 | 0 |
| 2, 3 | 3.21 | 0.003 | 0 |
| 4, 5 | 0.14 | 0.001 | 0.139 |
| 6 | 0.93 | 0.2415 | 0.6885 |
| 7, 8 | 0.77 | 0.2005 | 0.5695 |
| Total | 5.05 | 0.4475 | 1.397 |

The "mass (g)" in Table 1 indicates solids content of each fraction. The amount of baicalin glycosides was determined by subtracting the baicalin content from the solids content of a fraction in which baicalin or baicalin glycosides was qualitatively observed. The 80% ethanol fraction contained unreactedbaicalin (m/z 447) and baicalin glycosides (compounds containing one to three glucose molecules bonded to a sugar moiety of baicalin: baicalin monoglucoside (m/z 609), baicalin diglucoside (m/z 771), and baicalin triglucoside (m/z 933)).

Figure 13:
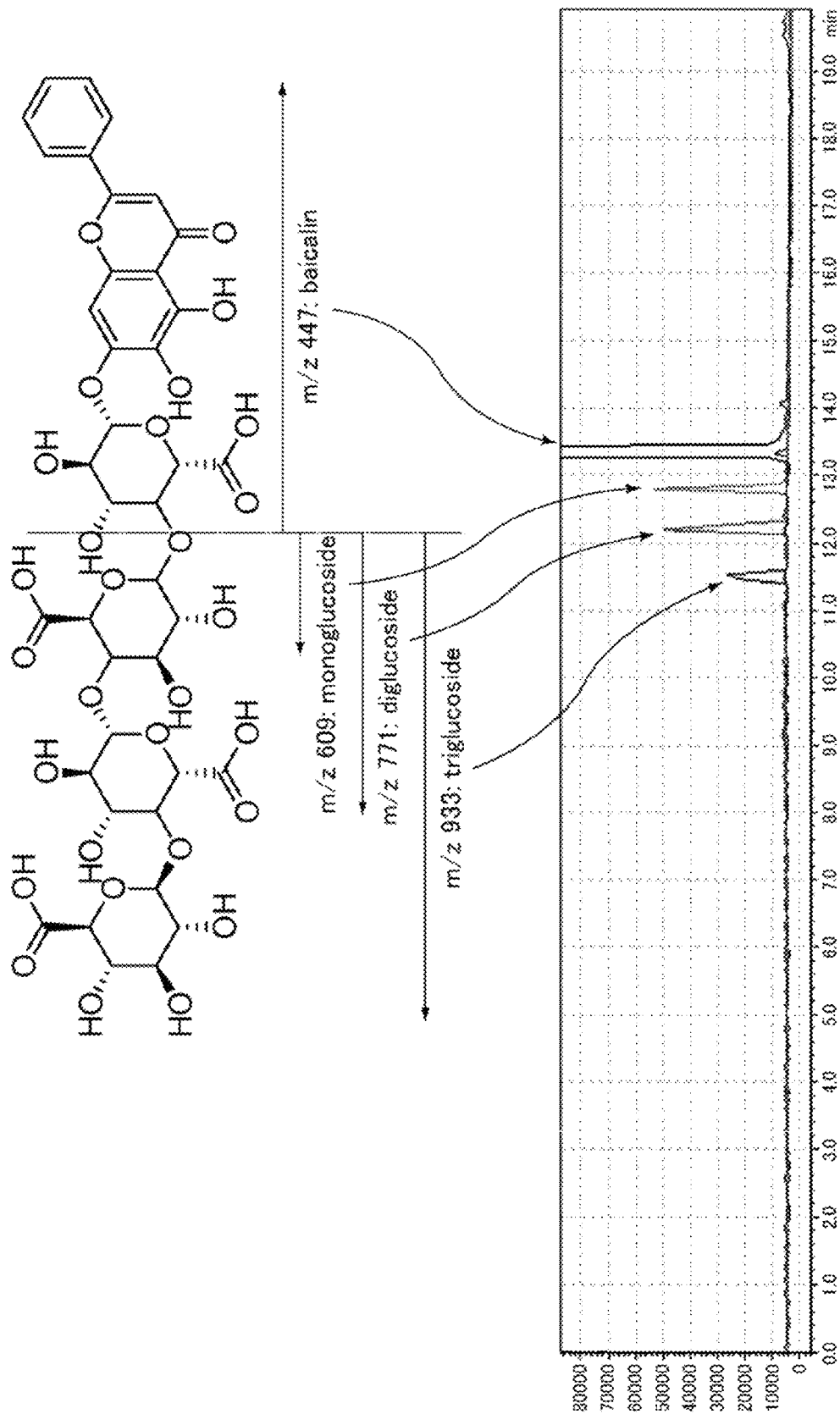
FIG. 13 is a chromatogram (SIM data) obtained by SIM mode LC-MS analysis of fractions containing glycated baicalin.

FIG. 13 is a chromatogram (SIM data) obtained by SIM mode LC-MS analysis of fractions containing baicalin glycosides. In FIG. 13, peaks indicate (from left to right) baicalin triglucoside (m/z 933), baicalin diglucoside (m/z 771), baicalin monoglucoside (m/z 609), and baicalin (m/z 447).

Example 4

Aldehyde-scavenging substances were screened.
(Construction of Assay System)

Aldehyde-scavenging ability of a candidate substance was evaluated based on how much the candidate substance added to a mixture of glyoxal (model aldehyde) and epicatechin (reaction substrate) can inhibit browning. The negative control was distilled water. As positive control, fractions 6, 7, and 8 (mixtures containing baicalin and baicalin glycosides (compounds containing one to three glucose molecules bonded to a sugar moiety of baicalin)) obtained in Preparation 1 were used.

A glyoxal aqueous solution (39% (v/v)) and epicatechin were used as reagents.

A sample solution was prepared by dissolving a candidate substance in water to adjust the total phenol amount derived from the candidate substance to 600 ppm. The total phenol amount was measured by the Folin-Denis method, using gallic acid as a standard substance. The amount of the candidate substance (the total phenol amount) was set such that the concentration of the candidate substance was about five time the concentration of the positive control at which the positive control exhibits browning inhibition activity.

A 1 mg/mL aqueous solution of epicatechin was prepared as a solution A. A glyoxal aqueous solution (39% v/v) (100 L) was diluted with distilled water to 300 mL to obtain a solution B. The solution A (60 μL), the sample solution (10 μL), distilled water (50 μL), and the solution B (60 L) were sequentially dispensed into a 96-well microplate. Plate seal (BMPCR-TS (BMBio)) was attached to the plate without gaps.

Accelerated aging was performed at 70° C. for 16 hours, and the area under the spectrum at 400 to 600 nm and the absorbance at 487 nm were measured.

Figure 14:
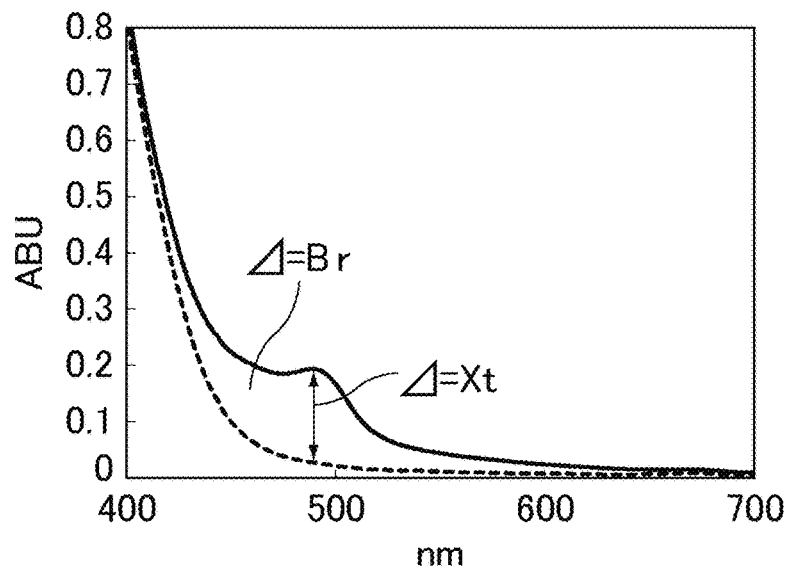
FIG. 14 is a diagram for explaining a Br value and an Xt value used in screening.

The amount of change in the visible absorbance before and after accelerated aging was calculated. A Br value (browning) and an Xt value (xanthylium) were set as indicators of browning inhibition activity. The Br value indicates the amount of change Δ in the area under the spectrum at 400 to 600 nm, and the Xt value indicates the amount of change Δ in the absorbance at 487 nm. FIG. 14 is a diagram for explaining the Br value and the Xt value used in screening. In FIG. 14, the solid line indicates the absorbance when a substance having an aldehyde-scavenging effect (a substance having a browning-inhibiting effect) was added, and the dashed line indicates the absorbance of the negative control.

When the Br value and the Xt value are higher than those of the negative control, it means that the candidate substance has a higher aldehyde-scavenging ability and a higher browning-inhibiting effect.

The following five kinds of compounds (Compounds (A-1) to (A-5)) were selected as candidate substances from the natural product database based on the structural features, and were evaluated for the aldehyde-scavenging ability by the above method. These compounds are all available from AnalytiCon.

[Chem. 11]

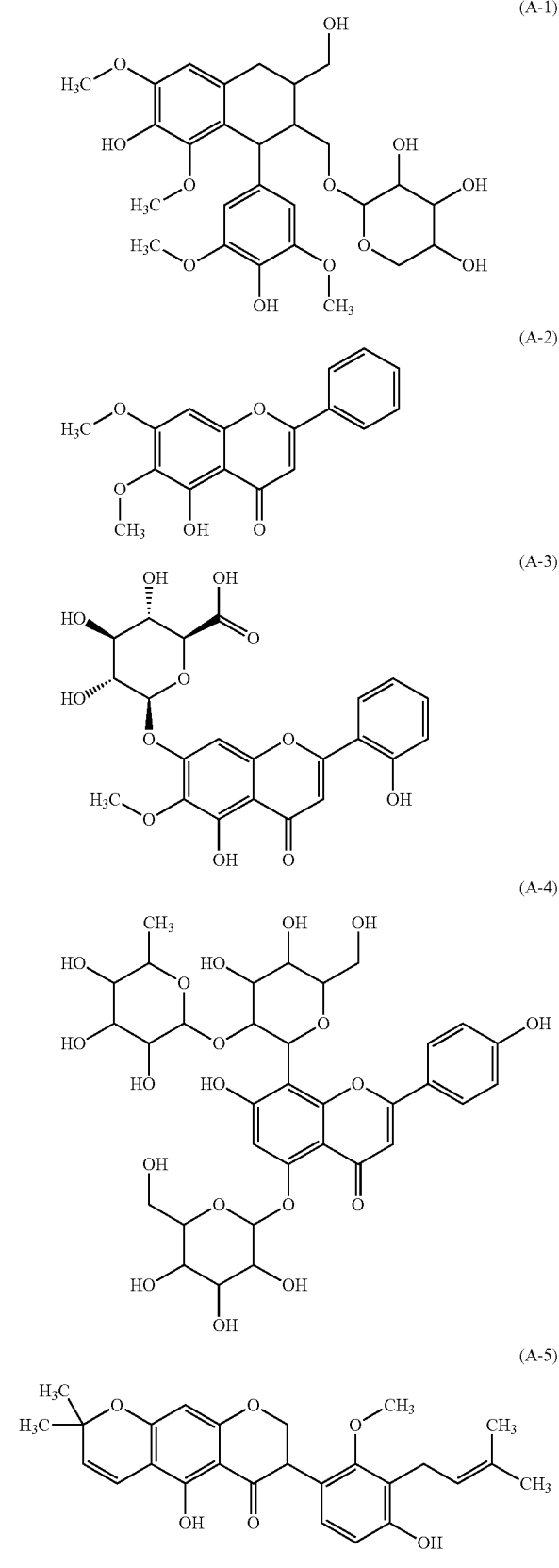

Figure 15:
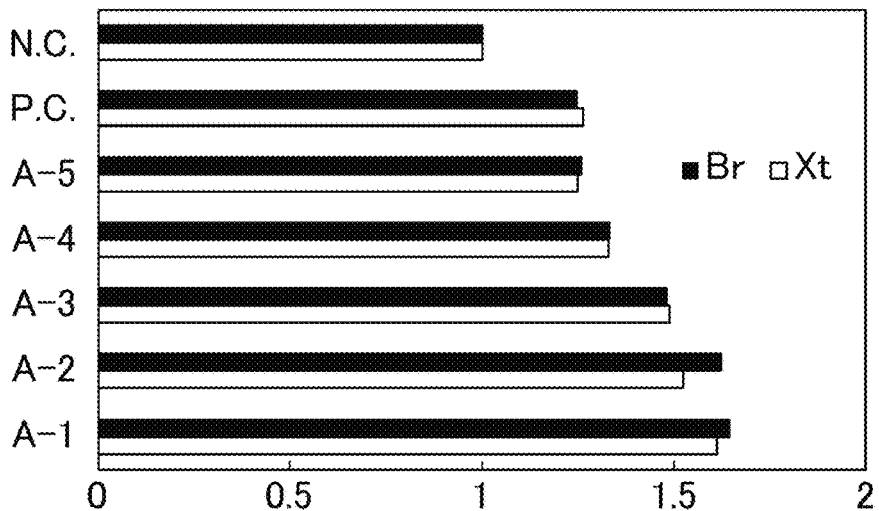
FIG. 15 is a graph showing results of browning-inhibiting effect evaluation of Compounds (A-1) to (A-5).

FIG. 15 shows results of browning-inhibiting effect evaluation of Compounds (A-1) to (A-5). In the results, Br values and Xt values of the candidate compounds are each expressed in ratios relative to a Br value and an Xt value of the negative control, respectively, which are both taken as 1. In FIG. 15, N.C. is negative control, and P.C. is positive control (baicalin and baicalin glycosides). The black bar indicates a Br value, and the white bar indicates an Xt value. The results shown in FIG. 15 are averages of three tests (N=3).

It was found that Compounds (A-1) to (A-5) each had the aldehyde-scavenging ability and exhibited the browning-inhibiting effect.

Example 5

Chafuroside A, icariin (Ark Pharm, Inc.), and scutellarin (Sigma-Aldrich) were used as candidate substances. Other than that, the aldehyde-scavenging ability and the browning-inhibiting effect were evaluated in the same manner as in Example 4. Chafuroside A is a compound represented by the following formula (B-1); icariin is a compound represented by the following formula (B-2); and scutellarin is a compound represented by the following formula (B-3).

[Chem. 12]

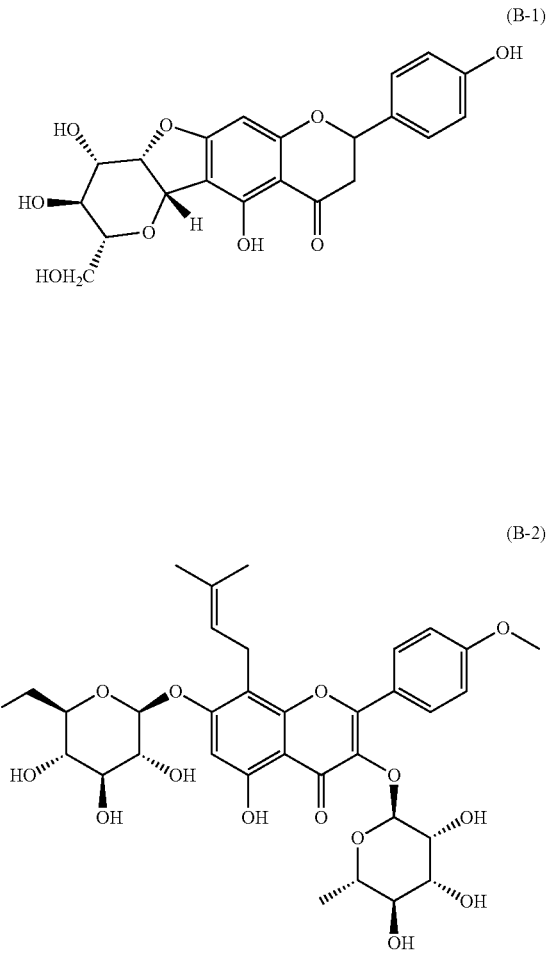

-continued

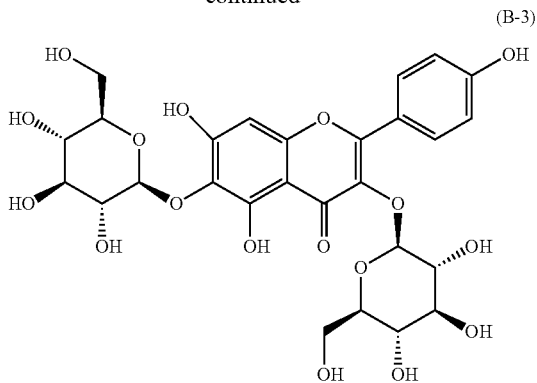

(B-3)

Figure 16:
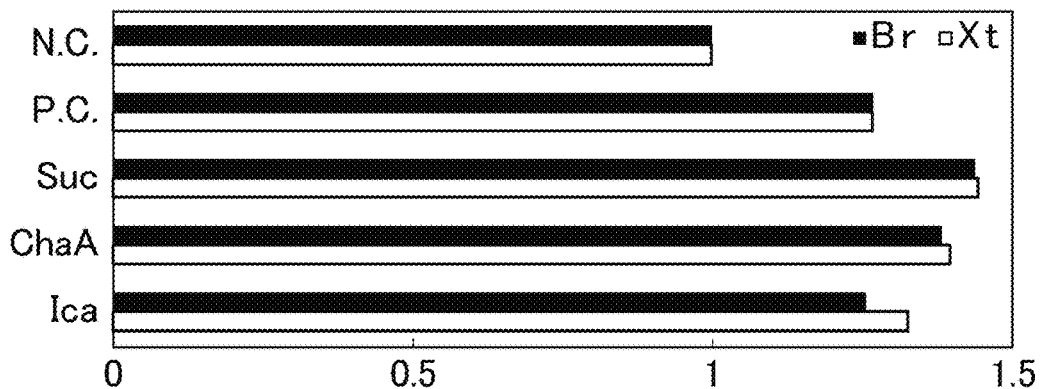
FIG. 16 is a graph showing results of browning-inhibiting effect evaluation of scutellarin, chafuroside A, and icariin.

FIG. 16 shows results of browning-inhibiting effect evaluation of scutellarin, chafuroside A, and icariin. In the results, Br values and Xt values of the candidate compounds are each expressed in ratios relative to a Br value and an Xt value of the negative control, respectively, which are both taken as 1. The results shown in FIG. 16 are averages of three tests. In FIG. 16, the black bar indicates a Br value, and the white bar indicates an Xt value. Suc is scutellarin, ChaA is chafuroside A, and Ica is icariin. N.C. is negative control (distilled water), and P.C. is positive control (baicalin and baicalin glycosides).

The aldehyde-scavenging effect was confirmed in chafuroside A, icariin, and scutellarin. These compounds exhibited poor water solubility at the concentration in this method, and undissolved parts were removed by filtration.

INDUSTRIAL APPLICABILITY

The present invention is useful in the food and beverage field and other fields.

The invention claimed is:

1. A polyphenol-containing food or drink product comprising a browning-inhibiting composition,
   wherein the browning-inhibiting composition comprises:
      at least one compound (1) selected from the group consisting of: baicalin monoglucoside, baicalin diglucoside and baicalin triglucoside, and
   the polyphenol in the polyphenol-containing food or drink product is catechins.

2. The polyphenol-containing food or drink product according to claim 1,
   wherein the amount of the compound (1) is 0.001 to 10% by mass relative to the polyphenol-containing food or drink product.

3. The polyphenol-containing food or drink product according to claim 1,
   wherein the polyphenol-containing food or drink product is a green tea beverage.

4. The polyphenol-containing food or drink product according to claim 1,
   wherein the polyphenol-containing food or drink product contains an aldehyde or a component producing an aldehyde by time-dependent degradation of the component.

5. A polyphenol-containing food or drink product comprising a browning-inhibiting composition,
   wherein the polyphenol-containing food or drink product is a green tea beverage,
   the polyphenol-containing food or drink product contains an aldehyde or a component producing an aldehyde by time-dependent degradation of the component,
   the browning-inhibiting composition comprises: at least one compound (1) selected from the group consisting of baicalin monoglucoside, baicalin diglucoside and baicalin triglucoside, and
   the amount of the compound (1) is 0.05 to 10% by mass relative to the green tea beverage.

* * * * *